United States Patent
Furukawa et al.

(10) Patent No.: US 11,540,702 B2
(45) Date of Patent: Jan. 3, 2023

(54) FLEXIBLE TUBE FOR ENDOSCOPE, ENDOSCOPIC MEDICAL DEVICE, RESIN COMPOSITION FOR COVERING FLEXIBLE TUBE SUBSTRATE FOR ENDOSCOPE, AND SET OF RESIN COMPOSITIONS FOR COVERING FLEXIBLE TUBE SUBSTRATE FOR ENDOSCOPE

(71) Applicant: FUJIFILM Corporation, Tokyo (JP)

(72) Inventors: Kazushi Furukawa, Kanagawa (JP); Yoshihiro Nakai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 409 days.

(21) Appl. No.: 16/702,615

(22) Filed: Dec. 4, 2019

(65) Prior Publication Data
US 2020/0107697 A1    Apr. 9, 2020

Related U.S. Application Data

(63) Continuation of application No. PCT/JP2018/024967, filed on Jun. 29, 2018.

(30) Foreign Application Priority Data

Jun. 30, 2017  (JP) .............................. JP2017-129906

(51) Int. Cl.
| | | |
|---|---|---|
| A61B 1/005 | (2006.01) | |
| C08K 5/1535 | (2006.01) | |
| C08K 5/17 | (2006.01) | |
| C08L 67/02 | (2006.01) | |
| C08L 75/04 | (2006.01) | |
| C08L 77/00 | (2006.01) | |

(52) U.S. Cl.
CPC ............ *A61B 1/005* (2013.01); *C08K 5/1535* (2013.01); *C08K 5/17* (2013.01); *C08L 67/02* (2013.01); *C08L 75/04* (2013.01); *C08L 77/00* (2013.01)

(58) Field of Classification Search
None
See application file for complete search history.

(56) References Cited

U.S. PATENT DOCUMENTS

| 4,664,115 A | 5/1987 | Ohachi |
| 5,685,825 A | 11/1997 | Takase et al. |
| 2009/0088727 A1 | 4/2009 | Mukai et al. |
| 2014/0037879 A1* | 2/2014 | Anker ...................... C08K 5/32 428/36.9 |
| 2016/0024343 A1 | 1/2016 | Nakai et al. |
| 2016/0088998 A1 | 3/2016 | Nagai et al. |

FOREIGN PATENT DOCUMENTS

| CN | 105455764 A | 4/2016 |
| EP | 2 980 466 A1 | 2/2016 |
| JP | 2003268168 A | 9/2003 |
| JP | 2010239981 A | 10/2010 |
| JP | 2013523209 A | 6/2013 |
| JP | 2014-188217 A | 10/2014 |
| JP | 2015-016261 A | 1/2015 |
| WO | 2011/119159 A1 | 9/2011 |
| WO | WO 2014/157375 | * 10/2014 |

OTHER PUBLICATIONS

An Office Action entitled Decision to Grant a Patent mailed by the Japanese Patent Office dated May 26, 2020, which corresponds to related Japanese Patent Application No. 2019-527094.

The partial supplementary European search report issued by the European Patent Office dated May 26, 2020, which corresponds to European Patent Application No. 18823845.5-1107 and is related to U.S. Appl. No. 16/702,615.

International Preliminary Report on Patentability issued in PCT/JP2018/024967; dated Jul. 12, 2019.

The extended European search report issued by the European Patent Office on Aug. 14, 2020, which corresponds to European Patent Application No. 18823845.5.

An Office Action mailed by China National Intellectual Property Administration dated Jul. 1, 2021 which corresponds to Chinese Patent Application No. 201880040267.X and is related to U.S. Appl. No. 16/702,615 with English language translation.

* cited by examiner

*Primary Examiner* — Robert T Butcher
(74) *Attorney, Agent, or Firm* — Studebaker & Brackett PC

(57) ABSTRACT

Provided is a flexible tube, for an endoscope, having a flexible tube substrate, for an endoscope, that is flexible and tubular and a resin layer covering the flexible tube substrate for an endoscope. The resin layer includes one or more layers, the layers including a layer A including a polyester elastomer (a) as a resin component, a hindered amine compound (b), and a particular compound (c). Also provided are an endoscopic medical device including the flexible tube for an endoscope and a resin composition and a set of resin compositions that are suitable for forming the resin layer of the flexible tube for an endoscope.

19 Claims, 4 Drawing Sheets

FLEXIBLE TUBE FOR ENDOSCOPE, ENDOSCOPIC MEDICAL DEVICE, RESIN COMPOSITION FOR COVERING FLEXIBLE TUBE SUBSTRATE FOR ENDOSCOPE, AND SET OF RESIN COMPOSITIONS FOR COVERING FLEXIBLE TUBE SUBSTRATE FOR ENDOSCOPE

CROSS-REFERENCE TO RELATED APPLICATIONS

This application is a Continuation of PCT International Application No. PCT/JP2018/024967 filed on Jun. 29, 2018, which claims priority under 35 U.S.C. § 119 (a) to Japanese Patent Application No. 2017-129906 filed in Japan on Jun. 30, 2017. Each of the above applications is hereby expressly incorporated by reference, in its entirety, into the present application.

BACKGROUND OF THE INVENTION

1. Field of the Invention

The present invention relates to flexible tubes for endoscopes, endoscopic medical devices, resin compositions for covering flexible tube substrates for endoscopes, and sets of resin compositions for covering flexible tube substrates for endoscopes.

2. Description of the Related Art

Endoscopes are medical devices for examination of a patient's body cavity. Since an endoscope is inserted and used in a body cavity, an endoscope that does not damage an organ or cause pain or discomfort to a patient is desirable. To meet this need, a spiral tube formed by spirally winding a flexible metal strip is used as a flexible tube that forms the insertion section of an endoscope. In addition, the periphery of the spiral tube is covered with a soft resin and is further covered with a topcoat layer so as not to cause stimulation or damage to the surface of a body cavity such as the esophagus or intestine.

Endoscopes are repeatedly used and therefore require cleaning and chemical disinfection after each use. Accordingly, technological development has been made to improve the chemical resistance of endoscopes. For example, JP2014-188217A describes a flexible tube, for an endoscope, having a resin layer composed of at least two layers, including a first layer including at least one elastomer or chain-extended derivative thereof selected from the group consisting of polyester elastomers, polyurethane elastomers, and polyamide elastomers and a second layer including chain-extended derivatives of at least two elastomers selected from the group consisting of polyester elastomers, polyurethane elastomers, and polyamide elastomers. This flexible tube is reported to have high resistance to washing solutions, to exhibit less change in physical properties with temperature (temperature dependence), and to have good adhesiveness between the resin layer and the topcoat layer.

JP2015-16261A describes a flexible tube, for an endoscope, having a resin layer including a layer containing a polyester elastomer and a hindered phenol compound or hindered amine compound. This flexible tube is reported to have the desired properties for endoscopes, including good flexibility, elasticity, and bending durability, as well as good resistance to various disinfectants.

SUMMARY OF THE INVENTION

Improvements have been made to flexible tubes for endoscopes so that they have the desired properties by techniques such as those described in the above patent documents. On the other hand, the requirements on the chemical resistance and other properties of flexible tubes for endoscopes are becoming more stringent year by year, and there is a need to alleviate, at a higher level, problems such as degraded appearance after chemical disinfection (after immersion in a disinfect), decreased interlayer adhesiveness, and decreased mechanical strength.

Accordingly, an object of the present invention is to provide a flexible tube, for an endoscope, that, upon exposure to a disinfectant, exhibits less degradation in appearance, can maintain good tensile strength, and can also sufficiently maintain high adhesiveness between the topcoat layer and the resin layer, an endoscopic medical device including such a flexible tube for an endoscope, and a resin composition and a set of resin compositions that are suitable for forming a resin layer of such a flexible tube for an endoscope.

The foregoing object is achieved by the following solutions:

(1) A flexible tube for an endoscope has a flexible tube substrate, for an endoscope, that is flexible and tubular and a resin layer covering the flexible tube substrate for an endoscope, wherein the resin layer includes one or more layers, the layers including a layer A including a polyester elastomer (a) as a resin component, a hindered amine compound (b), and a compound (c) represented by any of formulae (TS-I) to (TS-III):

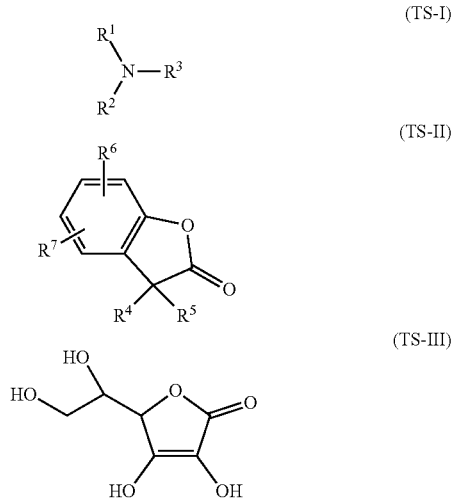

wherein in formula (TS-I), $R^1$ and $R^2$ represent a hydrogen atom, an aliphatic group, an acyl group, an aliphatic oxycarbonyl group, an aromatic oxycarbonyl group, an aliphatic sulfonyl group, or an aromatic sulfonyl group; $R^3$ represents an aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, or a hydroxy group; and $R^1$ and $R^2$, $R^2$ and $R^3$, or $R^1$ and $R^3$ may be attached to each other to form a 5- to 7-membered ring, but do not form a 2,2,6,6-tetraalkylpiperidine skeleton; provided that $R^1$ and $R^2$ are not simultaneously hydrogen atoms and have a total of 7 or more carbon atoms, and in formula (TS-II), $R^4$ to $R^7$ represent a hydrogen atom, an alkyl group having 1 to 20 carbon atoms, or an aryl group having 6 to 15 carbon atoms.

(2) In the flexible tube for an endoscope according to item (1), the amount of the polyester elastomer (a) is 50% by mass or more of the resin component in the layer A.

(3) In the flexible tube for an endoscope according to item (1) or (2), the layers include the layer A and a layer B including a polyurethane elastomer (d).

(4) In the flexible tube for an endoscope according to any one of items (1) to (3), the layer A further contains, as the resin component, at least one of a polyurethane elastomer (d) or a polyamide elastomer (e).

(5) In the flexible tube for an endoscope according to any one of items (1) to (4), the amount of the compound (c) is 0.01 to 5 parts by mass based on 100 parts by mass of the resin component in the layer A.

(6) In the flexible tube for an endoscope according to any one of items (1) to (5), the amount of the hindered amine compound (b) is 0.01 to 5 parts by mass based on 100 parts by mass of the resin component in the layer A.

(7) In the flexible tube for an endoscope according to any one of items (1) to (6), the ratio of the amount of the hindered amine compound (b) to the amount of the compound (c) is 1:50 to 50:1 by mass.

(8) In the flexible tube for an endoscope according to any one of items (1) to (7), the hindered amine compound (b) has a structural moiety represented by general formula (1):

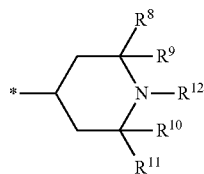

general formula (1)

wherein $R^8$ to $R^{11}$ represent a hydrogen atom or an alkyl group having 1 to 12 carbon atoms; $R^{12}$ represents a hydrogen atom, an alkyl group having 1 to 18 carbon atoms, or $-OR^{13}$, wherein $R^{13}$ represents a hydrogen atom or an alkyl group having 1 to 20 carbon atoms; and * represents a point of attachment.

(9) In the flexible tube for an endoscope according to any one of items (1) to (8), the hindered amine compound (b) is a compound represented by general formula (1-1) or a compound having a component represented by general formula (1-2):

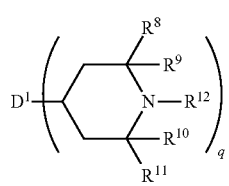

general formula (1-1)

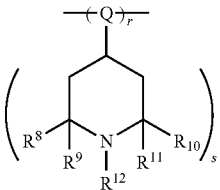

general formula (1-2)

wherein $R^8$ to $R^{12}$ have the same meanings as $R^8$ to $R^{12}$, respectively, in general formula (1) above; q represents an integer of 2 or more; $D^1$ represents a q-valent linking group; r represents a positive integer; Q represents an s+2-valent linking group; and s represents 1 or 2.

(10) In the flexible tube for an endoscope according to any one of items (1) to (9), the compound represented by formula (TS-I) above is a compound represented by formula (TS-IA) or (TS-IB):

(TS-IA)

(TS-IB)

wherein in formula (TS-IA), $R^1$ and $R^2$ have the same meanings as $R^1$ and $R^2$, respectively, in formula (TS-I) above; and $R^{b1}$ has the same meaning as $R^1$, and in formula (TS-IB), $R^{b2}$ to $R^{b4}$ represent an aliphatic group or an acyl group.

(11) The flexible tube for an endoscope according to any one of items (1) to (10) further has a topcoat layer.

(12) An endoscopic medical device includes the flexible tube for an endoscope according to any one of items (1) to (11).

(13) A resin composition for covering a flexible tube substrate for an endoscope includes a polyester elastomer (a), a hindered amine compound (b), and a compound (c) represented by any of formulae (TS-I) to (TS-III):

(TS-I)

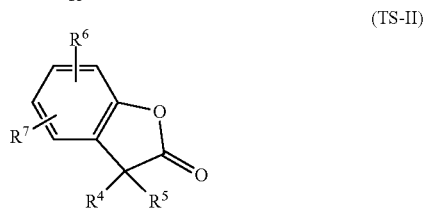

(TS-II)

-continued

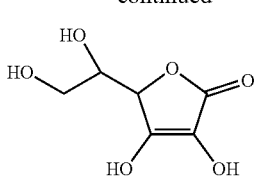
(TS-III)

wherein in formula (TS-I), $R^1$ and $R^2$ represent a hydrogen atom, an aliphatic group, an acyl group, an aliphatic oxycarbonyl group, an aromatic oxycarbonyl group, an aliphatic sulfonyl group, or an aromatic sulfonyl group; $R^3$ represents an aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, or a hydroxy group; and $R^1$ and $R^2$, $R^2$ and $R^3$, or $R^1$ and $R^3$ may be attached to each other to form a 5- to 7-membered ring, but do not form a 2,2,6,6-tetraalkylpiperidine skeleton; provided that $R^1$ and $R^2$ are not simultaneously hydrogen atoms and have a total of 7 or more carbon atoms, and in formula (TS-II), $R^4$ to $R^7$ represent a hydrogen atom, an alkyl group having 1 to 20 carbon atoms, or an aryl group having 6 to 15 carbon atoms.

(14) In the resin composition for covering a flexible tube substrate for an endoscope according to item (13), the ratio of the amount of the hindered amine compound (b) to the amount of the compound (c) is 1:50 to 50:1 by mass.

(15) A set of resin compositions for covering a flexible tube substrate for an endoscope includes a resin composition (A) including a polyester elastomer (a), a hindered amine compound (b), and a compound (c); and a resin composition (B) including at least one of a polyester elastomer (a1), a polyurethane elastomer (d), or a polyamide elastomer (e), wherein the compound (c) is represented by any of formulae (TS-I) to (TS-III):

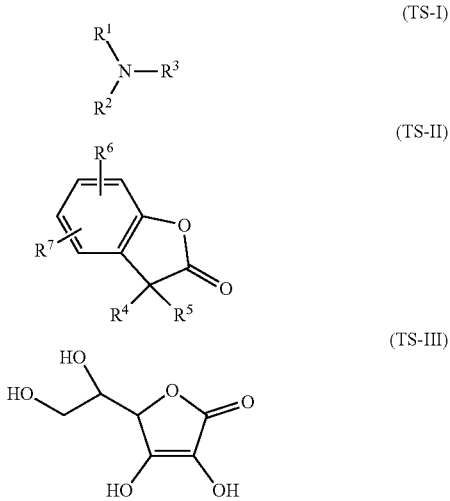

wherein in formula (TS-I), $R^1$ and $R^2$ represent a hydrogen atom, an aliphatic group, an acyl group, an aliphatic oxycarbonyl group, an aromatic oxycarbonyl group, an aliphatic sulfonyl group, or an aromatic sulfonyl group; $R^3$ represents an aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, or a hydroxy group; and $R^1$ and $R^2$, $R^2$ and $R^3$, or $R^1$ and $R^3$ may be attached to each other to form a 5- to 7-membered ring, but do not form a 2,2,6,6-tetraalkylpiperidine skeleton; provided that $R^1$ and $R^2$ are not simultaneously hydrogen atoms and have a total of 7 or more carbon atoms, and in formula (TS-II), $R^4$ to $R^7$ represent a hydrogen atom, an alkyl group having 1 to 20 carbon atoms, or an aryl group having 6 to 15 carbon atoms.

(16) In the set of resin compositions for covering a flexible tube substrate for an endoscope according to item (15), the ratio of the amount of the hindered amine compound (b) to the amount of the compound (c) is 1:50 to 50:1 by mass.

In the description of the present invention, a "resin component" present in a resin layer refers to an elastomer. "Resin component" may be hereinafter simply referred to as "resin".

In the description of the present invention, if there are a plurality of substituents, linking groups, or the like (hereinafter referred to as "substituent or the like") represented by a particular symbol, or if a plurality of substituents or the like are specified simultaneously or alternatively, it is meant that the individual substituents or the like may be the same or different. In addition, if a plurality of substituents or the like are adjacent to each other, it is meant that they may be linked or fused to each other to form a ring, even if not specified as such.

In the description of the present invention, if it is not explicitly specified whether a substituent (or linking group) is substituted or unsubstituted, it is meant that the group may have any substituent as long as the desired effect is achieved. This also applies if it is not explicitly specified whether a compound is substituted or unsubstituted.

The flexible tube for an endoscope according to the present invention has the desired sufficient chemical resistance; that is, upon exposure to a disinfectant, the flexible tube exhibits less degradation in appearance, can maintain good tensile strength, and can also sufficiently maintain a higher adhesiveness between the topcoat layer and the resin layer. The endoscopic medical device according to the present invention includes the flexible tube for an endoscope with the above superior properties. The resin composition for covering a flexible tube substrate for an endoscope and the set of resin compositions for covering a flexible tube substrate for an endoscope according to the present invention are suitable for use as a material for forming the resin layer of the flexible tube for an endoscope with the above properties.

DESCRIPTION OF THE PREFERRED EMBODIMENTS

Figure 1:
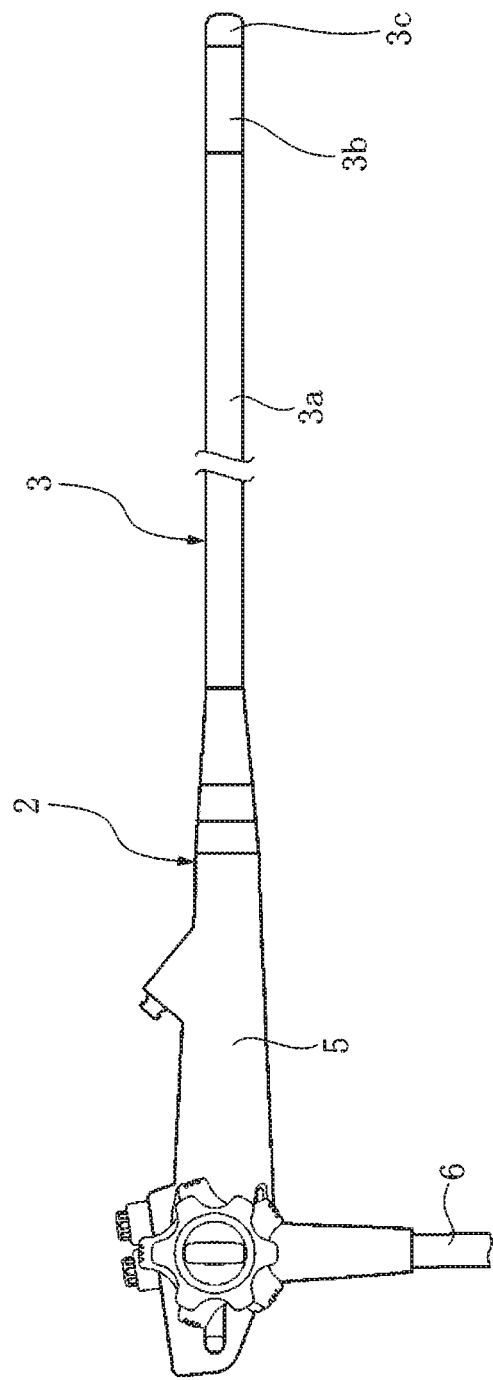
FIG. 1 is an external view illustrating the configuration of an electronic endoscope.

An electronic endoscope will now be described as an example of an endoscopic medical device according to a preferred embodiment of the present invention. Electronic endoscopes incorporate a flexible tube for an endoscope (a flexible tube for an endoscope may be hereinafter simply referred to as "flexible tube") and are widely used as medical devices. In the example shown in FIG. 1, an electronic endoscope 2 includes an insertion section 3 for insertion into a body cavity, a main-body operating section 5 connected to the proximal end portion of the insertion section 3, and a universal cord 6 for connection to a processor device and a light source device. The insertion section 3 is composed of a flexible tube 3a connected to the main-body operating section 5, an angle portion 3b connected to the flexible tube 3a, and a tip portion 3c connected to the distal end of the angle portion 3b and having an imaging device (not shown) built thereinto for imaging a body cavity. The flexible tube 3a, which accounts for most of the length of the insertion section 3, is flexible substantially over the entire length thereof. In particular, the portion to be inserted into an area such as a body cavity has a more flexible structure.

Flexible Tube

Figure 2:
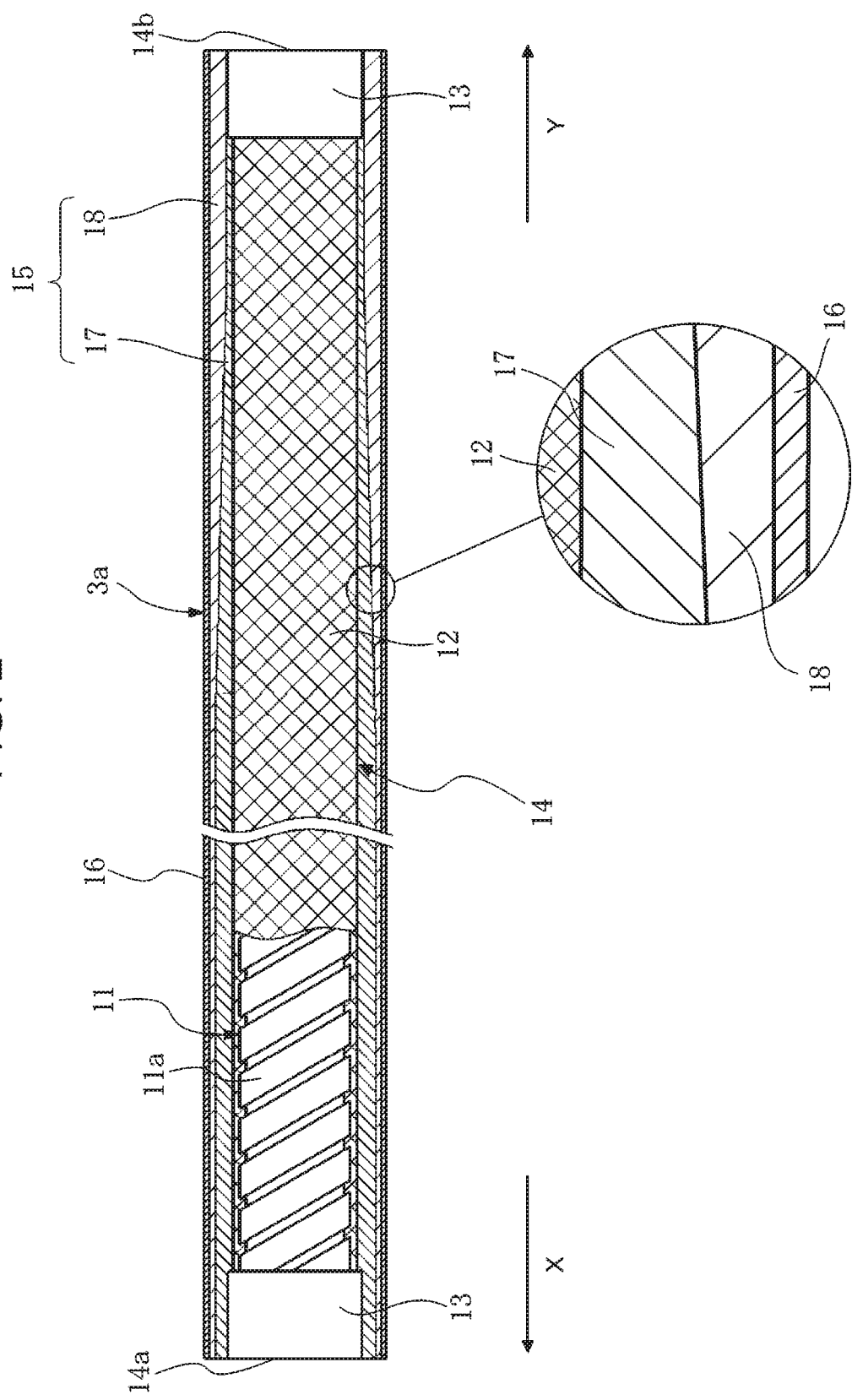
FIG. 2 is a partial sectional view schematically illustrating the configuration of a flexible tube for an endoscope.

As shown in FIG. 2, the flexible tube 3a (flexible tube for an endoscope) is composed of a flexible tube substrate 14 and a resin layer 15 covering the outer peripheral surface of the flexible tube substrate 14. The flexible tube substrate 14 includes a spiral tube 11 disposed on the innermost side and formed by spirally winding a metal strip 11a, a tubular net 12 covering the spiral tube 11 and formed by weaving metal wires, and caps 13 fitted to both ends. The outer surface of the resin layer 15 is covered with a chemical-resistant coat layer 16 such as one containing fluorine. Although the spiral tube 11 is shown as a single layer, it may be composed of two layers coaxially stacked on top of each other. To clearly illustrate the layer structure, the resin layer 15 and the coat layer 16 are shown as being thick relative to the diameter of the flexible tube substrate 14.

The resin layer 15 according to this embodiment covers the outer peripheral surface of the flexible tube substrate 14. The resin layer 15 has a two-layer configuration including an inner layer 17 covering the entire peripheral surface of the flexible tube substrate 14 about the axis thereof and an outer layer 18 covering the entire peripheral surface of the inner layer 17 about the axis thereof. A soft resin is used as the material for the inner layer 17, whereas a hard resin is used as the material for the outer layer 18. In other preferred embodiments of the present invention, the resin layer 15 may be composed of one layer (a layer A) or three or more layers (including the layer A).

In this embodiment, the resin layer 15 is formed with substantially uniform thickness in the longitudinal direction (axial direction) of the flexible tube substrate 14. The resin layer 15 has a thickness of, for example, 0.2 mm to 1.0 mm. The flexible tube 3a has an outer diameter D of, for example, 11 to 14 mm. The inner layer 17 and the outer layer 18 are formed such that the proportions of the thicknesses of the individual layers 17 and 18 relative to the total thickness of the resin layer 15 vary in the axial direction of the flexible tube substrate 14. Specifically, the proportion of the thickness of the inner layer 17 relative to the total thickness of the resin layer 15 is larger than that of the outer layer 18 on one end 14a side (distal side) of the flexible tube substrate 14 attached to the angle portion 3b. The inner layer 17 gradually becomes thinner from the end 14a toward the other end 14b side (proximal side) attached to the main-body operating section 5. The outer layer 18 is thicker than the inner layer 17 on the other end 14b side.

The proportion of the thickness of the inner layer 17 is maximum at the end 14a in this embodiment. The proportion of the thickness of the outer layer 18 is maximum at the other end 14b in this embodiment. The proportion of the thickness of the inner layer 17 to the thickness of the outer layer 18 is, for example, 9:1 at the end 14a and is, for example, 1:9 at the other end 14b. The proportion of the thickness of the inner layer 17 to the thickness of the outer layer 18 varies so as to be reversed between both ends 14a and 14b. Thus, there is a difference in hardness between the end 14a side and the other end 14b side of the flexible tube 3a, and the softness varies in the axial direction such that the flexible tube 3a is softer on the end 14a side and is harder on the other end 14b side. Preferably, the proportion of the thickness of the inner layer to the thickness of the outer layer is 5:95 to 40:60 (inner layer:outer layer) at one end and is 95:5 to 60:40 (inner layer:outer layer) at the other end.

As in the example above, it is preferred that the proportion of the thickness of the inner layer 17 to the thickness of the outer layer 18 be 5:95 to 95:5. Within this range, the amount of resin extruded can be more precisely controlled for the thinner layer.

The difference in modulus at 100% elongation, which is a measure of hardness after molding, between the soft resin used for the inner layer 17 and the hard resin used for the outer layer 18 is preferably 1 MPa or more, more preferably 3 MPa or more. The difference in melt viscosity at a molding temperature of 150° C. to 300° C., which is a measure of the fluidity of a molten resin, between the soft resin used for the inner layer 17 and the hard resin used for the outer layer 18 is preferably 2,500 Pa·s or less. This ensures that the resin layer 15 composed of the inner layer 17 and the outer layer 18 has both good molding accuracy and the required hardness difference between the distal side and the proximal side.

Method for Manufacturing Flexible Tube

An example method for manufacturing a flexible tube including a resin layer having a two-layer structure composed of an inner layer and an outer layer will hereinafter be described. A flexible tube including a resin layer composed of one layer or three or more layers can also be manufactured as in the method described below.

To form a resin layer composed of at least two layers including an inner layer and an outer layer, it is preferred to
  (i) provide a first resin material for the inner layer;
  (ii) provide a second resin material for the outer layer; and
  (iii) melt-kneading the first resin material and the second resin material and extrude them onto the periphery of the flexible tube substrate to cover the flexible tube substrate with the resin layer.

A method for manufacturing the flexible tube 3a (FIGS. 1 and 2) will now be described with reference to FIGS. 3 and 4. The resin layer 15 is preferably molded using a continuous molding machine. It is preferred to use a continuous molding machine 20 composed of known extrusion units 21 and 22 composed of parts such as hoppers and screws 21a and 22a, a head unit 23 for covering the outer peripheral surface of the flexible tube substrate 14 with the resin layer 15, a cooling unit 24, a transport unit 25 (a feed drum 28 and a take-up drum 29) that transports a continuous flexible tube substrate 31 to the head unit 23, and a control unit 26 that controls these units. The head unit 23 is preferably composed of a nipple 32, a die 33, and a support 34 fixedly supporting them. An example configuration of such a machine that can be used is shown in, for example, FIGS. 3 to 5 of JP2011-72391A.

The interior of the die 33 is preferably heated to a predetermined molding temperature. The molding temperature is preferably set within the range of 150° C. to 300° C. A soft resin 39 and a hard resin 40 can be heated to a high temperature by the heating temperature control of a heating unit within the machine. Additionally, as the rotational speeds of the screws 21a and 22a become higher, the soft resin 39 and the hard resin 40 can be heated to a higher temperature, thereby increasing their fluidity. During this process, the molding thicknesses of the inner layer 17 and the outer layer 18 can be adjusted by changing the amounts of the molten soft resin 39 and hard resin 40 ejected while transporting the continuous flexible tube substrate 31 at constant speed.

The process of molding the resin layer 15 onto the continuous flexible tube substrate 31 using the continuous molding machine 20 will now be described. When the continuous molding machine 20 performs the molding step, the molten soft resin 39 and hard resin 40 are extruded from the extrusion units 21 and 22 into the head unit 23. At the same time, the transport unit 25 operates to transport the continuous flexible tube substrate 31 to the head unit 23. During this process, the extrusion units 21 and 22 constantly extrude and feed the soft resin 39 and the hard resin 40 to the head unit 23, and the soft resin 39 and the hard resin 40 extruded from the extrusion units 21 and 22 into gates 35 and 36 merge together at an edge and, in a stacked state, are fed through a resin passage 38 to a molding passage 37. Thus, a two-layer molded resin layer 15 composed of a stack of an inner layer 17 made of the soft resin 39 and an outer layer 18 made of the hard resin 40 is formed.

The continuous flexible tube substrate 31 is composed of a plurality of flexible tube substrates 14 joined together. The resin layer 15 is continuously molded onto the plurality of flexible tube substrates 14 being transported through the molding passage 37. When the resin layer 15 is molded from the end 14a side (distal side) to the other end 14b side (proximal side) of one flexible tube substrate, the inner layer 17 is thick immediately after the extrusion units 21 and 22 start resin ejection. The proportion of the thickness of the outer layer 18 gradually increases over the middle portion toward the other end 14b side. It is preferred to control the amounts of the resins ejected in this way to achieve the above gradient in the proportion of the thickness of the resin layer 15.

A joint member 30, which is a connecting portion between two flexible tube substrates 14, is used for switching of the amounts of the resins ejected from the extrusion units 21 and 22 by the control unit 26. Specifically, the control unit 26 preferably switches the amounts of the resins ejected from the extrusion units 21 and 22 for transition from the proportion of the thickness on the other end 14b side (proximal side) of one flexible tube substrate 14 to the proportion of the thickness on the end 14a side (distal side) of the next flexible tube substrate 14. When the resin layer 15 is molded from the end 14a side to the other end 14b side of the next flexible tube substrate 14, it is preferred to similarly control the extrusion units 21 and 22 such that the outer layer gradually becomes thicker from one end side toward the other end side.

After the continuous flexible tube substrate 31 having the resin layer 15 molded to the rearmost end is detached from the continuous molding machine 20, the joint members 30 are detached from the flexible tube substrates 14 to separate the continuous flexible tube substrate 31 into the individual flexible tube substrates 14. The resin layer 15 on the separated flexible tube substrates 14 is then coated with the coat layer 16. Thus, flexible tubes 3a are finished. The finished flexible tubes 3a are transported to an electronic endoscope assembly step.

Resin Layer

Preferably, the resin layer of the flexible tube according to the present invention is composed of one or more layers, and the outermost layer of the resin layer is a layer A (a layer containing a polyester elastomer (a) (resin component), a hindered amine compound (b), and a compound (c) represented by any of formulae (TS-I) to (TS-III) described later). Here, the "outermost layer" of a resin layer having a single-layer structure refers to the resin layer itself, whereas the "outermost layer" of a resin layer having a multilayer structure composed of two or more layers refers to the surface layer of the resin layer of the flexible tube. The flexible tube according to the present invention preferably has another layer (e.g., a topcoat layer) outside the resin layer.

The hindered amine compound (b) may be hereinafter referred to as "compound (b)". The compound (c) represented by any of formulae (TS-I) to (TS-III) may be hereinafter referred to as "compound (c)".

Since the flexible tube according to the present invention has the resin layer with the above configuration, the flexible tube, after chemical disinfection, exhibits sufficiently reduced degradation in appearance, has good tensile strength, and can maintain a higher adhesiveness between the topcoat layer and the resin layer. Although the mechanism is not fully understood, one possible factor is that the compound (c) is localized to the surface of the layer A. That is, it is possible that the compound (c), which dissolves into the resin component together with the compound (b) during the process of molding the layer A, gradually becomes localized, because of its structure, to the surface of the layer A, for example, due to interaction with other molecules in the resin component. Consequently, it is possible that the compound (c) produces, for example, a protective effect (antioxidation effect) on the surface of the layer A, thus improving the chemical resistance.

If the resin layer of the flexible tube according to the present invention is composed of a plurality of layers, the flexible tube according to the present invention provides the above advantageous effects even if the layer A is not the outermost layer, but is an inner layer or interlayer. This is possibly because the compounds within the resin diffuse more easily during chemical disinfection, for example, due to the swelling of the resin, and the compound (c) present in the inner layer or interlayer diffuses to the surface of the outer layer and consequently produces, for example, a protective effect (antioxidation effect) on the surface of the outermost layer, thus improving the chemical resistance.

Polyester Elastomer (a)

The polyester elastomer (a) used in the present invention may be a common polyester elastomer that is applicable to the formation of flexible tubes.

Specifically, the polyester elastomer (a) used in the present invention is a copolymer composed of hard segments of a crystalline polyester and soft segments of a polyether or a polyester.

Examples of hard segments include polybutylene terephthalate and polyethylene terephthalate.

Examples of soft segments include polyalkylene glycols such as polytetramethylene glycol and polypropylene glycol, bisphenol A ethylene oxide adducts, bisphenol A propylene oxide adducts, and polyesters such as polycaprolactone.

In the present invention, a "polyester elastomer" may have urethane bonds, amide bonds, or both. In this case, of ester bonds, urethane bonds, and amide bonds, ester bonds are present in the largest number. Preferably, a "polyester elastomer" includes no urethane bond or amide bond in the molecule thereof.

Polyester elastomers (a) may be used alone or in combination.

Hindered Amine Compound (b)

The hindered amine compound (b) is preferably a compound having a structural moiety represented by general formula (1) below.

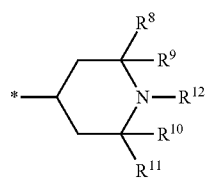

general formula (1)

In general formula (1), $R^8$ to $R^{11}$ represent a hydrogen atom or an alkyl group having 1 to 12 carbon atoms (preferably 1 to 8 carbon atoms, more preferably 1 to 5 carbon atoms). Specific examples of alkyl groups represented by $R^8$ to $R^{11}$ include methyl, ethyl, n-butyl, isopropyl, s-butyl, t-butyl, t-pentyl, t-hexyl, and t-octyl. Preferably, $R^8$ to $R^{11}$ are primary (linear) alkyl groups. More preferably, all of $R^8$ to $R^{11}$ are primary (linear) alkyl groups (particularly preferably methyl groups).

In general formula (1), $R^{12}$ represents a hydrogen atom, an alkyl group having 1 to 18 carbon atoms (preferably 1 to 10 carbon atoms, more preferably 1 to 5 carbon atoms, even more preferably 1 to 3 carbon atoms, further preferably 1 or 2 carbon atoms), or $-OR^{13}$, where $R^{13}$ represents a hydrogen atom or a linear, branched, or cyclic alkyl group having 1 to 20 carbon atoms (preferably 1 to 12 carbon atoms). In particular, $R^{13}$ is preferably a hydrogen atom, which results in a higher chemical resistance.

In general formula (1), * represents a point of attachment.

The compound having a structural moiety represented by general formula (1) is preferably a compound represented by general formula (1-1) below or a compound having a component (preferably a repeating unit) represented by general formula (1-2) below.

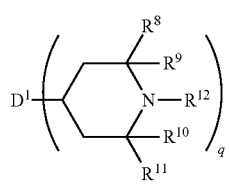

general formula (1-1)

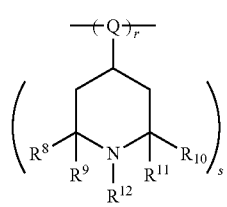

general formula (1-2)

In the formulae, $R^8$ to $R^{12}$ have the same meanings as $R^8$ to $R^{12}$, respectively, in general formula (1) above, and preferred ranges are also the same; q represents an integer of 2 or more; $D^1$ represents a q-valent linking group; s represents 1 or 2; r represents a positive integer, preferably within the range of degrees of polymerization described later; and Q represents an s+2-valent linking group such as a group including an aromatic hydrocarbon group, a group including an imino group ($NR^N$), or a group including a triazine linking group. Specific examples of $R^N$ include hydrogen atoms, alkyl groups having 1 to 20 carbon atoms, and piperidyl-containing groups represented by general formula (1).

The linking group represented by $D^1$ preferably has a molecular weight of 100 to 1,000, more preferably 180 to 600. The linking group represented by Q preferably has a molecular weight of 100 to 1,000, more preferably 180 to 600.

More preferably, the compound having a structural moiety represented by general formula (1) is a compound represented by any of formulae (1-A) to (1-C), (1-E), (1-G), and (1-H) below, a polymer or oligomer having a repeating unit represented by formula (1-D) below (preferably a polymer or oligomer having a repeating unit represented by any of formulae (1D1) to (1D3)), or a polymer or oligomer having a repeating unit represented by formula (1-F) below.

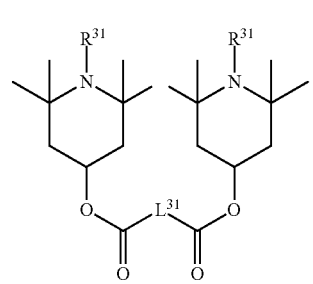

(1-A)

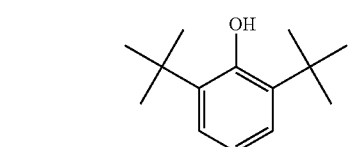

(1-B)

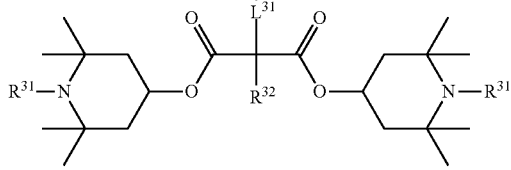

(1-C)

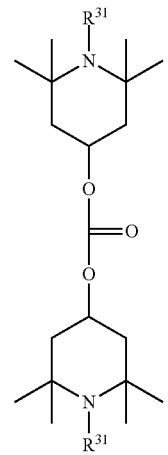

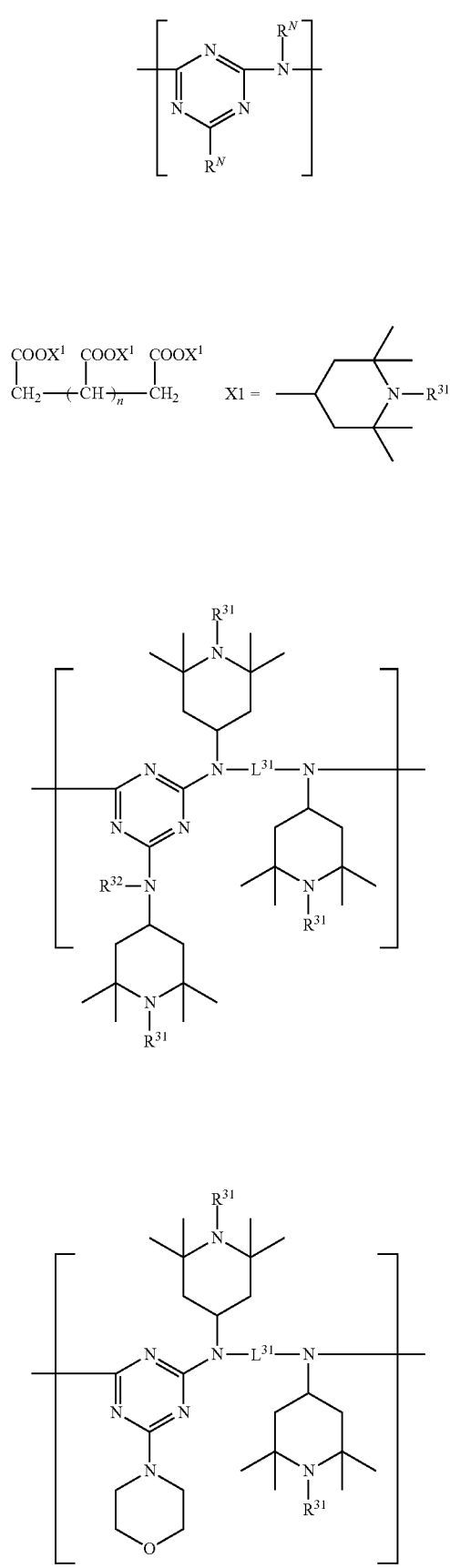
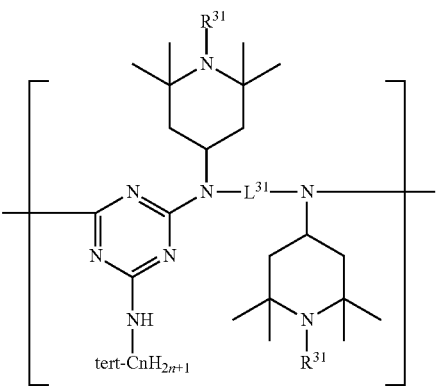
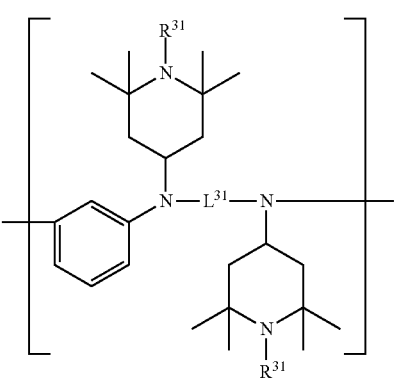
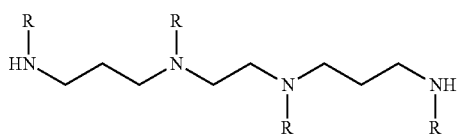
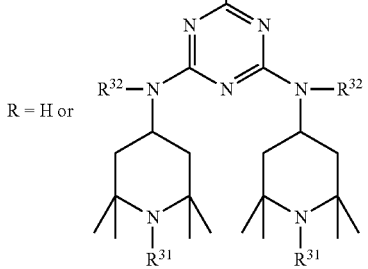
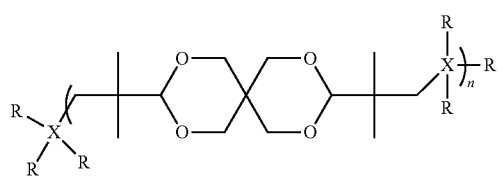
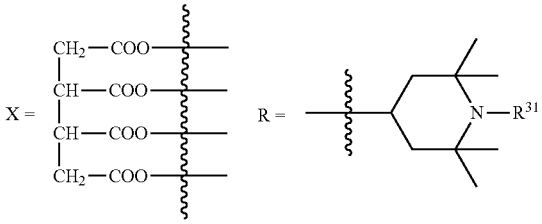

In the formulae, $R^{31}$ has the same meaning as $R^{12}$ in general formula (1), and preferred forms are also the same.

$R^{32}$ represents a hydrogen atom or an alkyl group having 1 to 20 carbon atoms (preferably 1 to 12 carbon atoms, more preferably 1 to 8 carbon atoms, even more preferably 1 to 6 carbon atoms). $L^{31}$ represents a single bond or an alkylene group having 1 to 20 carbon atoms (preferably 1 to 10 carbon atoms). $R^N$ has the same meaning as $R^N$ in general formula (1-2). n represents an integer of 1 to 20 (preferably 1 to 10) (in formula (1D3), n represents an integer of 4 to 20 (preferably 4 to 10)).

In formula (1-G), at least one R is not H, but a group including triazine. In formula (1-H), the wavy lines represent a point of attachment.

If the compound having a structural moiety represented by general formula (1) is a polymer or oligomer, the number of repeating units (degree of polymerization) is preferably 2 to 100, more preferably 2 to 50, even more preferably 2 to 10. The terminal structures of the polymer or oligomer may each be, for example, but not limited to, a hydrogen atom, a substituted or unsubstituted amino group, or a substituted or unsubstituted triazyl group.

Hindered amine compounds (b) may be used alone or in combination.

Compound (c) Represented by Any of Formulae (TS-I) to (TS-III)

(1) Compound (c) Represented by Formula (TS-I)

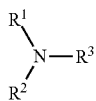

(TS-I)

In formula (TS-I), $R^1$ and $R^2$ represent a hydrogen atom, an aliphatic group, an acyl group, an aliphatic oxycarbonyl group, an aromatic oxycarbonyl group, an aliphatic sulfonyl group, or an aromatic sulfonyl group.

$R^3$ represents an aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, or a hydroxy group.

$R^1$ and $R^2$, $R^2$ and $R^3$, or $R^1$ and $R^3$ may be attached to each other to form a 5- to 7-membered ring, but do not form a 2,2,6,6-tetraalkylpiperidine skeleton.

In formula (TS-1), $R^1$ and $R^2$ are not simultaneously hydrogen atoms and have a total of 7 or more carbon atoms.

The aliphatic groups in formula (TS-I) (including those forming part of any substituent in formula (TS-1)) refer to alkyl, alkenyl, and alkynyl groups. The alkyl, alkenyl, and alkynyl groups may be linear, branched, or cyclic.

The alkyl groups preferably have 1 to 20 carbon atoms, more preferably 1 to 18 carbon atoms. However, the alkyl groups have at least 3 carbon atoms if they are branched or cyclic. This also applies to the alkenyl and alkynyl groups.

The alkenyl groups preferably have 2 to 20 carbon atoms, more preferably 2 to 18 carbon atoms.

The alkynyl groups preferably have 2 to 20 carbon atoms, more preferably 2 to 18 carbon atoms. The aliphatic groups may have at least one of the following substituents T.

Substituents T

Halogen Atoms

Fluorine, Chlorine, Bromine, and Iodine Atoms

Alkyl Groups (Linear, Branched, or Cyclic Substituted or Unsubstituted Alkyl Groups)

Linear or branched alkyl groups (preferably substituted or unsubstituted alkyl groups having 1 to 30 carbon atoms, e.g., methyl, ethyl, propyl, isopropyl, t-butyl, octyl, eicosyl, 2-chloroethyl, 2-cyanoethyl, and 2-ethylhexyl)

Cycloalkyl groups (preferably substituted or unsubstituted cycloalkyl groups having 3 to 30 carbon atoms, e.g., cyclohexyl, cyclopentyl, and 4-dodecylcyclohexyl)

Bicycloalkyl groups (preferably substituted or unsubstituted bicycloalkyl groups having 5 to 30 carbon atoms, i.e., monovalent groups derived by removing one hydrogen atom from bicycloalkanes having 5 to 30 carbon atoms, e.g., bicyclo[1.2.2]heptan-2-yl and bicyclo[2.2.2]octan-3-yl)

In the present invention, cyclic alkyl groups include, in addition to cycloalkyl groups and bicycloalkyl groups (bicyclic groups), polycycloalkyl groups such as tricycloalkyl, tetracycloalkyl, and pentacycloalkyl groups.

Preferred forms of alkyl groups forming the substituents described below (e.g., the alkyl groups of alkylthio groups) include those listed as the substituents T.

Alkenyl groups (linear, branched, or cyclic substituted or unsubstituted alkenyl groups)

Linear or branched alkenyl groups (preferably substituted or unsubstituted alkenyl groups (having 2 to 30 carbon atoms), e.g., vinyl, allyl, prenyl, geranyl, and oleyl)

Cycloalkenyl groups (preferably substituted or unsubstituted cycloalkenyl groups having 3 to 30 carbon atoms, i.e., monovalent groups derived by removing one hydrogen atom from cycloalkenes having 3 to 30 carbon atoms, e.g., 2-cyclopenten-1-yl and 2-cyclohexen-1-yl)

Bicycloalkenyl groups (substituted or unsubstituted bicycloalkenyl groups, preferably substituted or unsubstituted bicycloalkenyl groups having 5 to 30 carbon atoms, i.e., monovalent groups derived by removing one hydrogen atom from bicycloalkenes having one double bond, e.g., bicyclo[2.2.1]hept-2-en-1-yl and bicyclo[2.2.2]oct-2-en-4-yl))

Alkynyl Group (Linear, Branched, or Cyclic Substituted or Unsubstituted Alkynyl Groups)

Preferably, substituted or unsubstituted alkynyl groups having 2 to 30 carbon atoms, e.g., ethynyl, propargyl, and trimethylsilylethynyl Aryl Groups Preferably, substituted or unsubstituted aryl groups having 6 to 40 carbon atoms (more preferably 6 to 30 carbon atoms, particularly preferably 6 to 20 carbon atoms), e.g., phenyl, p-tolyl, naphthyl, m-chlorophenyl, and o-hexadecanoylaminophenyl (more preferably phenyl and naphthyl, particularly preferably phenyl). Substituted aryl groups may be fused with an aliphatic ring, another aromatic ring, or a heterocycle.

Heterocyclic Groups

Preferably, monovalent groups derived by removing one hydrogen atom from 5- or 6-membered substituted or unsubstituted heterocyclic compounds (including aromatic heterocyclic compounds and nonaromatic heterocyclic compounds), more preferably 5- or 6-membered substituted or unsubstituted aromatic heterocyclic groups having 3 to 30 carbon atoms, e.g., 2-furyl, 2-thienyl, 2-pyrimidinyl, and 2-benzothiazolyl Cyano Groups Hydroxy Groups Nitro Groups Carboxy Groups Alkoxy Groups Preferably, substituted or unsubstituted alkoxy groups having 1 to 30 carbon atoms, e.g., methoxy, ethoxy, isopropoxy, t-butoxy, octyloxy, and 2-methoxyethoxy Aryloxy Groups Preferably, substituted or unsubstituted aryloxy groups having 6 to 30 carbon atoms, e.g., phenoxy, 2-methylphenoxy, 4-t-butylphenoxy, 3-nitrophenoxy, 2-tetradecanoylaminophenoxy, and p-methoxyphenoxy Silyloxy Groups Preferably, substituted or unsubstituted silyloxy groups having 3 to 20 carbon atoms, e.g., trimethylsilyloxy and t-butyldimethylsilyloxy Heterocyclic Oxy Groups Preferably, substituted or unsubstituted heterocyclic oxy groups having 2 to 30 carbon atoms, e.g., 1-phenyltetrazole-5-oxy and 2-tetrahydropyranyloxy Acyloxy Groups Preferably, formyloxy groups, substituted or unsubstituted alkylcarbonyloxy groups having 2 to 30 carbon atoms, and substituted or unsubstituted arylcarbonyloxy groups having 6 to 30 carbon atoms, e.g., formyloxy, acetyloxy, pivaloyloxy, stearoyloxy, benzoyloxy, and p-methoxyphenylcarbonyloxy Carbamoyloxy Groups Preferably, substituted or unsubstituted carbamoyloxy groups having 1 to 30 carbon atoms, e.g., N,N-dimethylcarbamoyloxy, N,N-diethylcarbamoyloxy, morpholinocarbonyloxy, N,N-dioctylaminocarbonyloxy, and N-octylcarbamoyloxy Alkoxycarbonyloxy Groups Preferably, substituted or unsubstituted alkoxycarbonyloxy groups having 2 to 30 carbon atoms, e.g., methoxycarbonyloxy, ethoxycarbonyloxy, t-butoxycarbonyloxy, and octyloxycarbonyloxy Aryloxycarbonyloxy Groups Preferably, substituted or unsubstituted aryloxycarbonyloxy groups having 7 to 30 carbon atoms, e.g., phenoxycarbonyloxy, p-methoxyphenoxycarbonyloxy, and p-hexadecyloxyphenoxycarbonyloxy Amino Groups Preferably, amino groups, substituted or unsubstituted alkylamino groups having 1 to 30 carbon atoms, and substituted or unsubstituted anilino groups having 6 to 30 carbon atoms (specific examples of substituents for substituted amino groups and substituted anilino groups include aliphatic groups, aryl groups, acyl groups, aliphatic sulfonyl groups, and aromatic sulfonyl groups), e.g., amino, methylamino, dimethylamino, anilino, N-methyl-anilino, and diphenylamino Acylamino Groups Preferably, formylamino groups, substituted or unsubstituted alkylcarbonylamino groups having 2 to 30 carbon atoms, and substituted or unsubstituted arylcarbonylamino groups having 6 to 30 carbon atoms, e.g., formylamino, acetylamino, pivaloylamino, lauroylamino, benzoylamino, and 3,4,5-trioctyloxyphenylcarbonylamino Aminocarbonylamino Groups Preferably, substituted or unsubstituted aminocarbonylamino groups having 1 to 30 carbon atoms, e.g., carbamoylamino, N,N-dimethylaminocarbonylamino, N,N-diethylaminocarbonylamino, and morpholinocarbonylamino Alkoxycarbonylamino Groups Preferably, substituted or unsubstituted alkoxycarbonylamino groups having 2 to 30 carbon atoms, e.g., methoxycarbonylamino, ethoxycarbonylamino, t-butoxycarbonylamino, octadecyloxycarbonylamino, and N-methyl-methoxycarbonylamino Aryloxycarbonylamino Groups Preferably, substituted or unsubstituted aryloxycarbonylamino groups having 7 to 30 carbon atoms, e.g., phenoxycarbonylamino, p-chlorophenoxycarbonylamino, and m-octyloxyphenoxycarbonylamino Sulfamoylamino Groups Preferably, substituted or unsubstituted sulfamoylamino groups having 0 to 30 carbon atoms, e.g., sulfamoylamino, N,N-dimethylaminosulfonylamino, and N-octylaminosulfonylamino Alkylsulfonylamino and Arylsulfonylamino Groups Preferably, substituted or unsubstituted alkylsulfonylamino groups having 1 to 30 carbon atoms and substituted or unsubstituted arylsulfonylamino groups having 6 to 30 carbon atoms, e.g., methylsulfonylamino, butylsulfonylamino, phenylsulfonylamino, 2,3,5-trichlorophenylsulfonylamino, and p-methylphenylsulfonylamino Sulfanyl Groups Alkylthio Groups Preferably, substituted or unsubstituted alkylthio groups having 1 to 30 carbon atoms, e.g., methylthio, ethylthio, hexadecylthio, and octylthio Arylthio Groups Preferably, substituted or unsubstituted arylthio groups having 6 to 30 carbon atoms, e.g., phenylthio, p-chlorophenylthio, m-methoxyphenylthio, and p-methoxyphenylthio Heterocyclic Thio Groups Preferably, substituted or unsubstituted heterocyclic thio groups having 2 to 30 carbon atoms, e.g., 2-benzothiazolylthio and 1-phenyltetrazol-5-ylthio Sulfamoyl Groups Preferably, substituted or unsubstituted sulfamoyl groups having 0 to 30 carbon atoms, e.g., N-ethylsulfamoyl, N-(3-dodecyloxypropyl)sulfamoyl, N,N-dimethylsulfamoyl, N-acetylsulfamoyl, N-benzoylsulfamoyl, and N—(N'-phenylcarbamoyl)sulfamoyl Sulfo Groups Alkylsulfinyl and Arylsulfinyl Groups Preferably, substituted or unsubstituted alkylsulfinyl groups having 1 to 30 carbon atoms and substituted or unsubstituted arylsulfinyl groups having 6 to 30 carbon atoms, e.g., methylsulfinyl, ethylsulfinyl, phenylsulfinyl, and p-methylphenylsulfinyl Alkylsulfonyl and Arylsulfonyl Groups Preferably, substituted or unsubstituted alkylsulfonyl groups having 1 to 30 carbon atoms and substituted or unsubstituted arylsulfonyl groups having 6 to 30 carbon atoms, e.g., methylsulfonyl, ethylsulfonyl, butylsulfonyl, phenylsulfonyl, and p-methylphenylsulfonyl Acyl Groups Preferably, formyl groups, substituted or unsubstituted alkylcarbonyl groups having 2 to 30 carbon atoms, substituted or unsubstituted arylcarbonyl groups having 7 to 30 carbon atoms, and substituted or unsubstituted heterocyclic carbonyl groups having 4 to 30 carbon atoms (in which any of the carbon atoms of the heterocycle is attached to the carbon atom of the carbonyl group), e.g., acetyl, pivaloyl, 2-chloroacetyl, stearoyl, benzoyl, p-octyloxyphenylcarbonyl, 2-pyridylcarbonyl, 2-furylcarbonyl, and (meth)acryloyl Aryloxycarbonyl Groups Preferably, substituted or unsubstituted aryloxycarbonyl groups having 7 to 30 carbon atoms, e.g., phenoxycarbonyl, o-chlorophenoxycarbonyl, m-nitrophenoxycarbonyl, and p-t-butylphenoxycarbonyl Alkoxycarbonyl Groups Preferably, substituted or unsubstituted alkoxycarbonyl groups having 2 to 30 carbon atoms, e.g., methoxycarbonyl, ethoxycarbonyl, t-butoxycarbonyl, hexadecyloxycarbonyl, and octadecyloxycarbonyl Carbamoyl Groups Preferably, substituted or unsubstituted carbamoyl groups having 1 to 30 carbon atoms, e.g., carbamoyl, N-methylcarbamoyl, N,N-dimethylcarbamoyl, N,N-dioctylcarbamoyl, and N-(methylsulfonyl)carbamoyl Arylazo and Heterocyclic Azo Groups Preferably, substituted or unsubstituted arylazo groups having 6 to 30 carbon atoms and substituted or unsubstituted heterocyclic azo groups having 3 to 30 carbon atoms, e.g., phenylazo, p-chlorophenylazo, and 5-ethylthio-1,3,4-thiadiazol-2-ylazo Imide Groups Preferably, N-succinimide and N-phthalimide Phosphino Groups Preferably, substituted or unsubstituted phosphino groups having 2 to 30 carbon atoms, e.g., dimethylphosphino, diphenylphosphino, and methylphenoxyphosphino Phosphinyl Groups Preferably, phosphinyl groups and substituted or unsubstituted phosphinyl groups having 2 to 30 carbon atoms, e.g., phosphinyl, dioctyloxyphosphinyl, and diethoxyphosphinyl Phosphinyloxy Groups Preferably, substituted or unsubstituted phosphinyloxy groups having 2 to 30 carbon atoms, e.g., diphenoxyphosphinyloxy and dioctyloxyphosphinyloxy Phosphinylamino Groups Preferably, substituted or unsubstituted phosphinylamino groups having 2 to 30 carbon atoms, e.g., dimethoxyphosphinylamino and dimethylaminophosphinylamino Silyl Groups Preferably, substituted or unsubstituted silyl groups having 3 to 30 carbon atoms, e.g., trimethylsilyl, t-butyldimethylsilyl, and phenyldimethylsilyl Of the above substituents T, those having hydrogen atoms may have their hydrogen atoms replaced by the above substituents. Examples of such substituents include alkylcarbonylaminosulfonyl groups, arylcarbonylaminosulfonyl groups, alkylsulfonylaminocarbonyl groups, and arylsulfonylaminocarbonyl groups. Examples thereof include methylsulfonylaminocarbonyl, p-methylphenylsulfonylaminocarbonyl, acetylaminosulfonyl, and benzoylaminosulfonyl.

Specific examples of acyl groups in formula (TS-I) include the acyl groups listed as the substituents T.

Specific examples of aliphatic oxycarbonyl groups in formula (TS-I) include the alkoxycarbonyl groups listed as the substituents T.

Specific examples of aromatic oxycarbonyl groups in formula (TS-I) include the aryloxycarbonyl groups listed as the substituents T.

Specific examples of aliphatic sulfonyl groups in formula (TS-I) include the alkylsulfonyl groups listed as the substituents T.

Specific examples of aromatic sulfonyl groups in formula (TS-I) include the arylsulfonyl groups listed as the substituents T.

Specific examples of aliphatic oxy groups in formula (TS-I) include the alkoxy groups listed as the substituents T.

Specific examples of aromatic oxy groups in formula (TS-I) include the aryloxy groups listed as the substituents T.

Specific examples of aliphatic thio groups in formula (TS-I) include the alkylthio groups listed as the substituents T.

Specific examples of aromatic thio groups in formula (TS-I) include the arylthio groups listed as the substituents T.

Specific examples of acyloxy groups in formula (TS-I) include the acyloxy groups listed as the substituents T.

Specific examples of aliphatic oxycarbonyloxy groups in formula (TS-I) include the alkoxycarbonyloxy groups listed as the substituents T.

Specific examples of aromatic oxycarbonyloxy groups in formula (TS-I) include the aryloxycarbonyloxy groups listed as the substituents T.

Specific examples of substituted amino groups in formula (TS-I) include the substituted amino groups listed as the substituents T.

The heterocyclic groups in formula (TS-I) preferably include a 5- or 6-membered saturated or unsaturated heterocycle. The heterocycle may be fused with an aliphatic ring, an aromatic ring, or another heterocycle. Examples of heteroatoms in the heterocycle include B, N, O, S, Se, and Te. Preferred heteroatoms are N, O, and S. The heterocycle preferably has a free valence (monovalent) on its carbon atom (the heterocyclic group is attached on its carbon atom to another group). The heterocyclic group preferably has 1 to 40 carbon atoms, more preferably 1 to 30 carbon atoms, even more preferably 1 to 20 carbon atoms. Examples of saturated heterocycles include pyrazolidine rings, pyrrolidine rings, morpholine rings, 2-bora-1,3-dioxolane rings, and 1,3-thiazolidine rings (excluding piperidine rings). Examples of unsaturated heterocycles include imidazole rings, thiazole rings, benzothiazole rings, benzoxazole rings, benzotriazole rings, benzoselenazole rings, pyridine rings, pyrimidine rings, and quinoline rings. The heterocyclic group may have a substituent. Examples of substituents include the above substituents T.

In formula (TS-I), $R^1$ and $R^2$ have a total of 7 or more carbon atoms, preferably 7 to 70 carbon atoms, more preferably 7 to 40 carbon atoms.

Examples of compounds represented by formula (TS-I) above that may be used in the present invention include compounds represented by general formula (I) of JP1994-97332B (JP-H6-97332B), general formula (I) of JP1994-97334B (JP-H6-97334B), general formula (I) of JP1990-148037A (JP-H2-148037A), general formula (I) of JP1990-150841A (JP-H2-150841A), general formula (I) of JP1990-181145A (JP-H2-181145A), general formula (I) of JP1991-266836A (JP-H3-266836A), general formula (IV) of JP1992-350854A (JP-H4-350854A), and general formula (I) of JP1993-61166A (JP-H5-61166A).

The compound represented by formula (TS-I) above is preferably a compound represented by general formula (TS-IA) or (TS-IB) below.

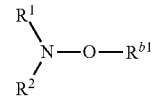

(TS-IA)

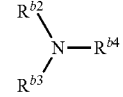

(TS-IB)

In general formula (TS-IA), $R^1$ and $R^2$ have the same meanings as $R^1$ and $R^2$, respectively, in formula (TS-I) above; and $R^{b1}$ has the same meaning as $R^1$.

In general formula (TS-IB), $R^{b2}$ to $R^{b4}$ represent an aliphatic group or an acyl group.

Specific examples of compounds represented by formula (TS-I) above are given below, although these examples are not intended to limit the present invention.

(I-1)
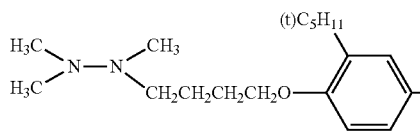

(I-2)
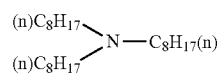

(I-3)
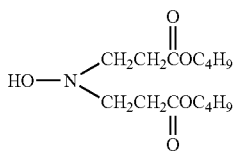

(I-4)
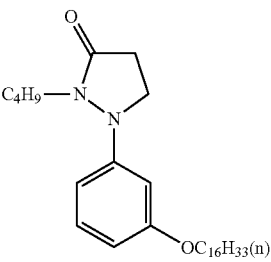

(I-5)
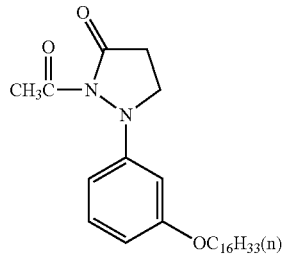

(I-6)
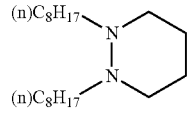

(I-7)
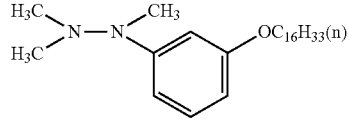

(I-8)
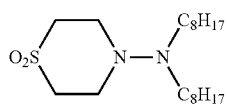

(I-9)
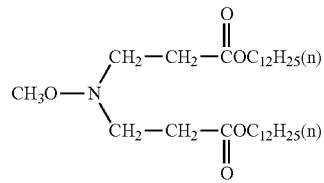

(I-10)
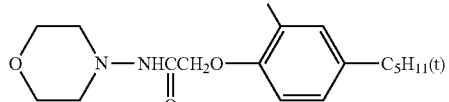

(I-11)

(I-12)
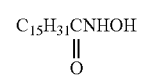

(I-13)
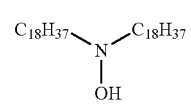

(I-14)

(I-15)
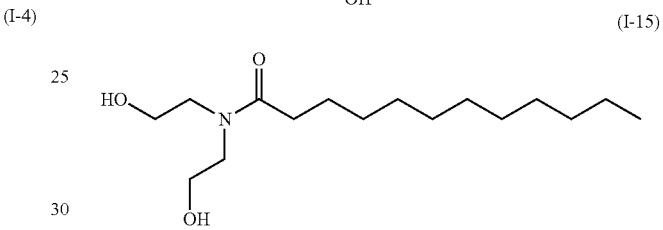

Compounds (c) represented by formula (TS-I) may be used alone or in combination.

(2) Compound (c) Represented by Formula (TS-II)

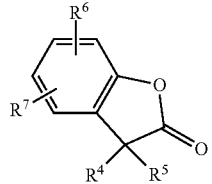

(TS-II)

In formula (TS-II), $R^4$ to $R^7$ represent a hydrogen atom, an alkyl group having 1 to 20 carbon atoms, an aralkyl group having 7 to 20 carbon atoms, or an aryl group having 6 to 15 carbon atoms. The substituents represented by $R^4$ to $R^7$ may have at least one of the above substituents T.

In formula (TS-II), the alkyl groups having 1 to 20 carbon atoms may be linear or branched alkyl groups. Examples of such alkyl groups include methyl, ethyl, propyl, isopropyl, butyl, isobutyl, pentyl, 2-ethylbutyl, hexyl, heptyl, octyl, 2-ethylhexyl, nonyl, decyl, dodecyl, tetradecyl, octadecyl, eicosyl, benzyl, 2,6-di-t-butyl-4-methylbenzyl, phenethyl, phenylpropyl, naphthylmethyl, and 2-phenylisopropyl. If the alkyl groups have a substituent, the above number of carbon atoms includes the number of carbon atoms of this substituent.

In formula (TS-II), the aryl groups having 6 to 15 carbon atoms may be, for example, phenyl, tolyl, or naphthyl. If the aryl groups have a substituent, the above number of carbon atoms includes the number of carbon atoms of this substituent.

In formula (TS-II), $R^4$ and $R^5$ are preferably a combination of a hydrogen atom and an aryl group having 7 to 20 carbon atoms. Of these, $R^4$ and $R^5$ are preferably a combination of a hydrogen atom and an aryl group having 8 to 20 carbon atoms, more preferably a combination of a hydrogen atom and an aryl group having 8 to 18 carbon atoms, particularly preferably a combination of a hydrogen atom and 3,4-dimethylphenyl.

In formula (TS-II), of the above groups, $R^6$ and $R^7$ are preferably alkyl groups having 1 to 20 carbon atoms, more preferably alkyl groups having 2 to 20 carbon atoms, even preferably alkyl groups having 3 to 20 carbon atoms, particularly preferably t-butyl.

Specific examples of compounds (c) represented by formula (TS-II) include the following compounds, although these examples are not intended to limit the present invention.

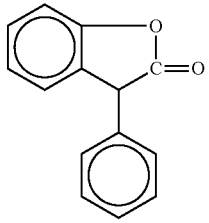
(A-1)

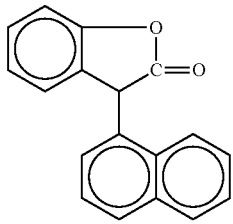
(A-2)

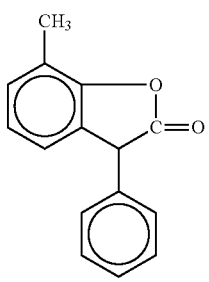
(A-3)

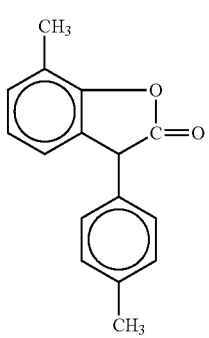
(A-4)

-continued

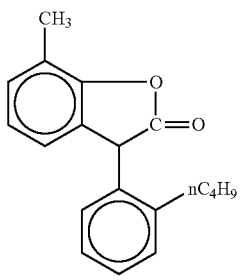
(A-5)

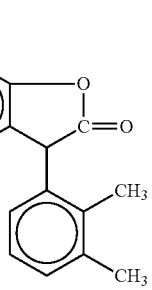
(A-6)

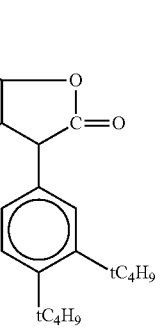
(A-7)

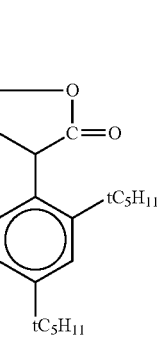
(A-8)

-continued
(A-9)
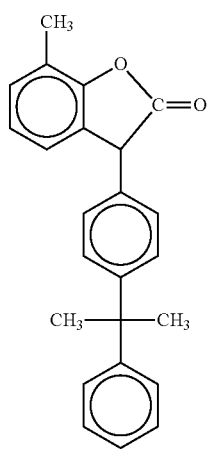
(A-10)
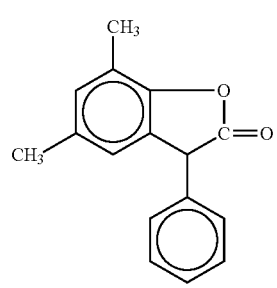
(A-11)
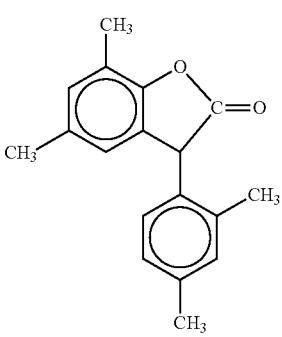
(A-12)
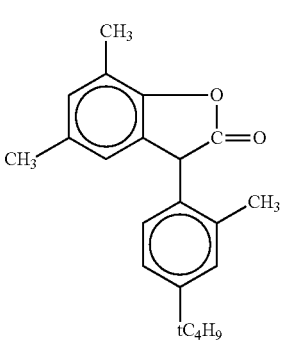
(A-13)
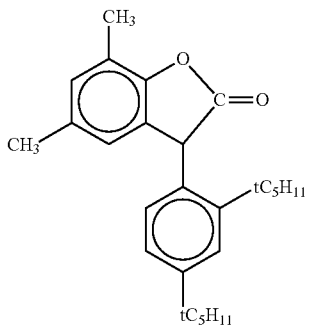
(A-14)
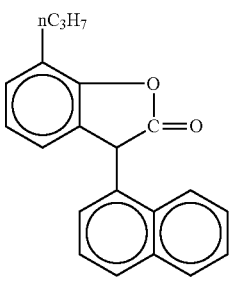
(A-15)
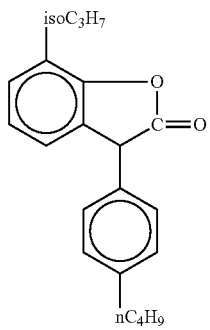
(A-16)
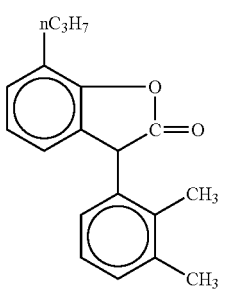
(A-17)
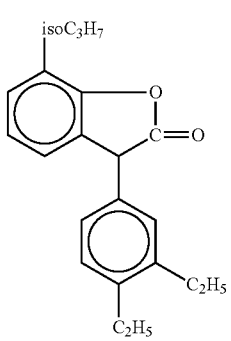

-continued
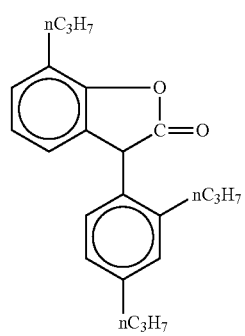 (A-18)
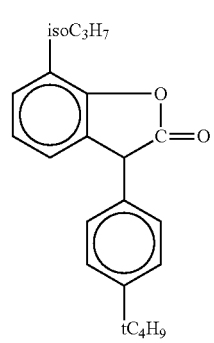 (A-19)
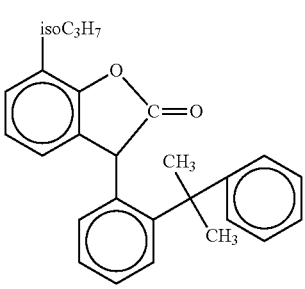 (A-20)
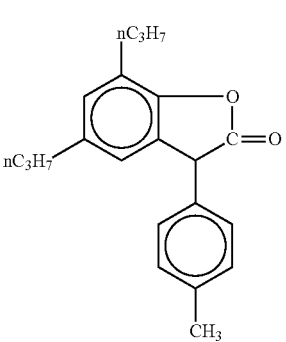 (A-21)
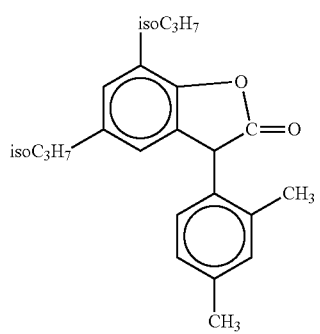 (A-22)
-continued
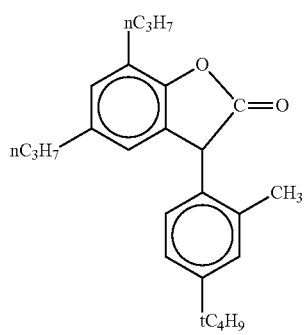 (A-23)
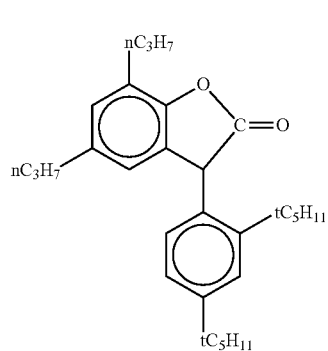 (A-24)
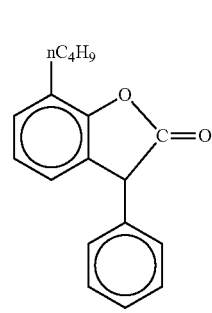 (A-25)
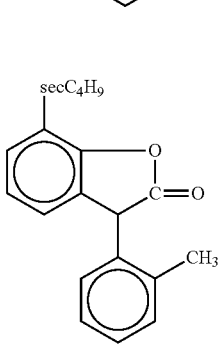 (A-26)
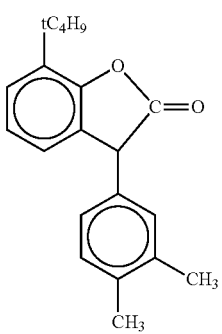 (A-27)

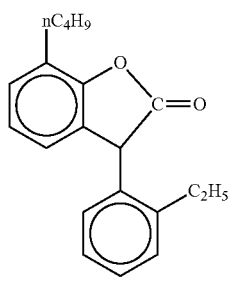
(A-28)
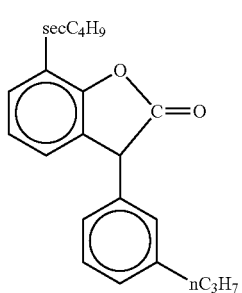
(A-29)
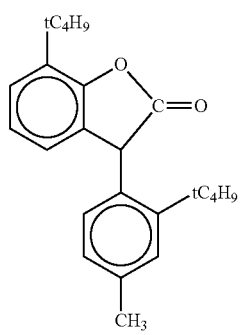
(A-30)
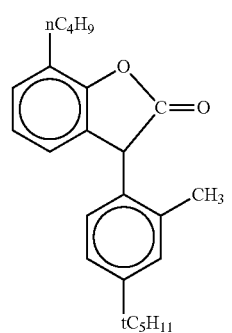
(A-31)
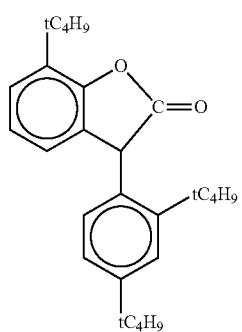
(A-32)
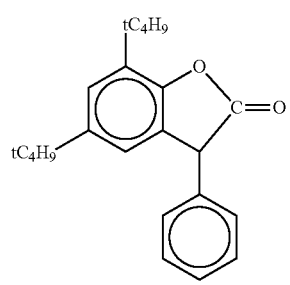
(A-33)
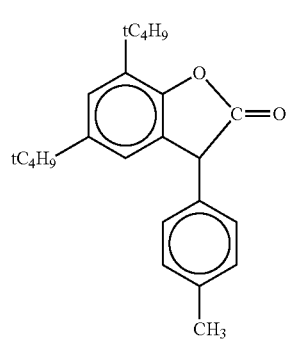
(A-34)
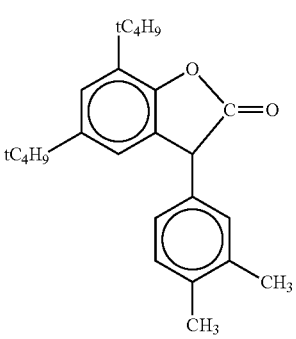
(A-35)
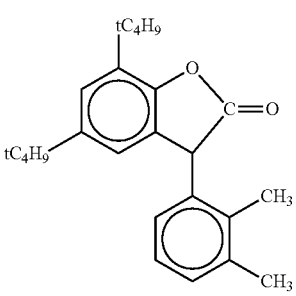
(A-36)
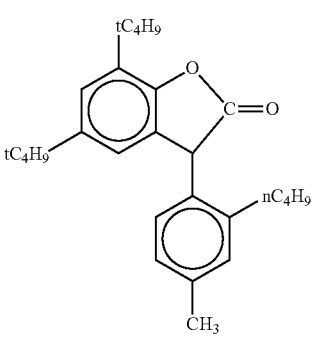
(A-37)

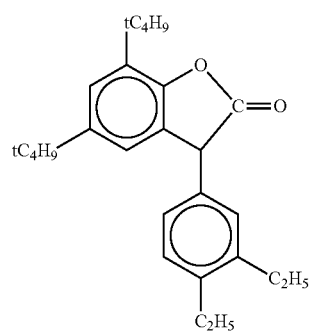
(A-38)
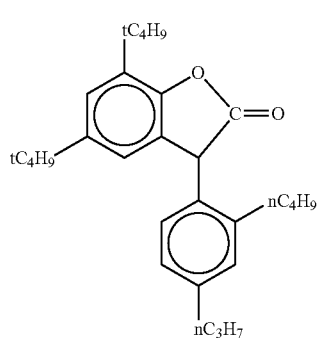
(A-39)
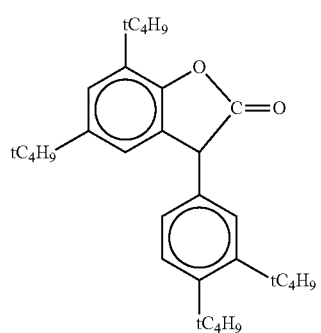
(A-40)
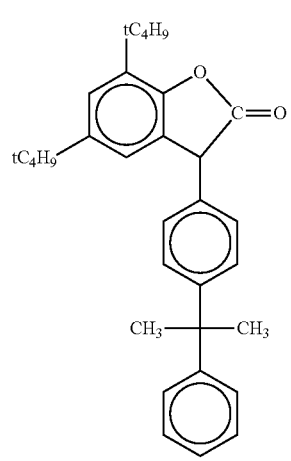
(A-41)
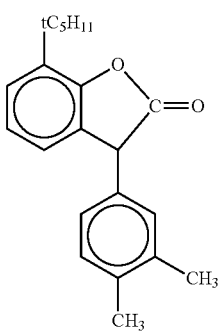
(A-42)
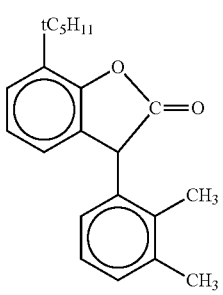
(A-43)
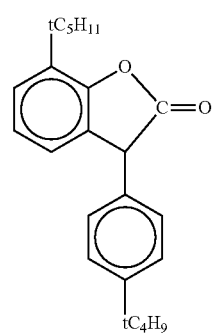
(A-44)
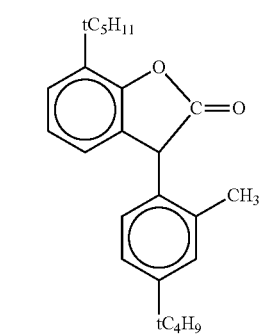
(A-45)
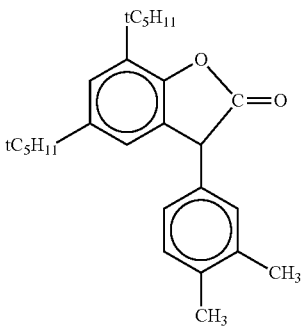
(A-46)

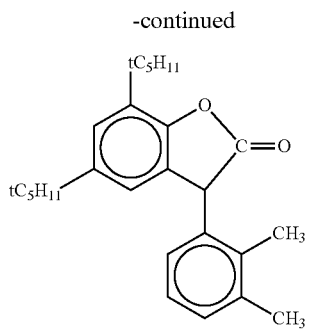
(A-47)

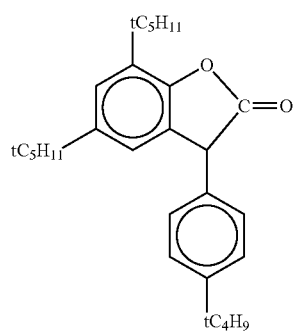
(A-48)

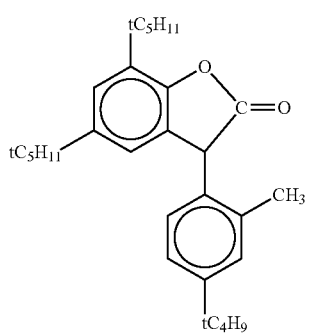
(A-49)

Compounds (c) represented by formula (TS-II) may be used alone or in combination.

Examples of compounds (c) represented by any of formulae (TS-I) to (TS-III) that may be used include those commercially available.

Compounds (c) represented by any of formulae (TS-I) to (TS-III) may be used alone or in combination.

The amount of the polyester elastomer (a) is preferably 50% by mass or more, more preferably 55% by mass or more, even more preferably 60% by mass or more, further preferably 65% by mass or more, of the resin component forming the layer A (preferably the outermost layer) of the resin layer.

Although the amount of the polyester elastomer may be 100% by mass of the resin component forming the layer A, the amount of the polyester elastomer is preferably 95% by mass or less, more preferably 90% by mass or less, even more preferably 85% by mass or less. If the amount of the polyester elastomer (a) in the layer A falls within the above preferred range, and a soft resin is blended as the remainder, better flexibility can be achieved.

The layer A of the resin layer may have the polyester elastomer (a) alone as the resin component or may further include a component other than the polyester elastomer (a) as the resin component. If the layer A of the resin layer further includes a component other than the polyester elastomer (a) as the resin component, the remainder of the resin component excluding the polyester elastomer (a) preferably includes, as a softer resin, at least one of a polyurethane elastomer (d) or a polyamide elastomer (e).

The polyurethane elastomer (d) may be a common polyurethane elastomer that is applicable to the formation of flexible tubes. The polyamide elastomer (e) may be a common polyamide elastomer that is applicable to the formation of flexible tubes. In the present invention, the polyurethane elastomer (d) preferably has no amide bond, and the polyamide elastomer (e) preferably has no urethane bond.

The inclusion of at least one of the polyurethane elastomer (d) or the polyamide elastomer (e) can improve the adhesiveness between the layer A and another layer forming at least one of the flexible tube substrate for an endoscope or the resin layer (the flexible tube substrate for an endoscope and/or the resin layer). If the resin component in the layer A of the resin layer includes at least one of the polyurethane elastomer (d) or the polyamide elastomer (e), the total amount of at least one of the polyurethane elastomer (d) or the polyamide elastomer (e) is preferably 5% by mass or more, more preferably 10% by mass or more, even more preferably 20% by mass or more. On the other hand, the total amount of at least one of the polyurethane elastomer (d) or the polyamide elastomer (e) is preferably 50% by mass or less, more preferably 40% by mass or less, even more preferably 35% by mass or less, of the resin component in the layer A of the resin layer. The inclusion of at least one of the polyurethane elastomer (d) or the polyamide elastomer (e) in the above amount can improve the adhesiveness while maintaining desirable elasticity and flexibility and maintaining sufficient chemical resistance.

Polyurethane elastomers (d) may be used alone or in combination. Polyamide elastomers (e) may be used alone or in combination.

In a preferred form of the layer A of the resin layer, the compound (c) is preferably present in an amount of 0.01 parts by mass or more, more preferably 0.05 parts by mass or more, based on 100 parts by mass of the resin component. On the other hand, the amount of the compound (c) is preferably 7 parts by mass or less, more preferably 5 parts by mass or less, based on 100 parts by mass of the resin component. If the amount of the compound (c) falls within the above range, a layer A that provides the desired effect while allowing less of this compound to migrate from the resin can be obtained.

In a preferred form of the layer A of the resin layer, the hindered amine compound (b) is preferably present in an amount of 0.01 parts by mass or more, more preferably 0.1 parts by mass or more, even more preferably 1 part by mass or more, based on 100 parts by mass of the resin component. The upper limit is preferably 7 parts by mass or less, more preferably 5 parts by mass or less. If the amount of the hindered amine compound (b) falls within the above range, a layer A that provides the desired effect while allowing less of this compound to migrate from the resin can be obtained.

In a preferred form of the layer A of the resin layer, the ratio of the amount of the hindered amine compound (b) to the amount of the compound (c) is preferably, by mass, 1:50 to 50:1, more preferably 1:30 to 20:1, even more preferably 1:20 to 10:1, particularly preferably 1:5 to 10:1. If the ratio of the amounts of these additives falls within the above range by mass, the antagonism between the additives can be inhibited, thus further improving the properties such as chemical resistance.

If the resin layer is composed of a plurality of layers, at least one layer other than the layer A (preferably the outermost layer) preferably contains at least one of the polyester elastomer (a), the polyurethane elastomer (d), or the polyamide elastomer (e) (the polyester elastomer (a), the polyurethane elastomer (d), and/or the polyamide elastomer (e)) (this layer is hereinafter referred to as "layer B"). More preferably, the layer B contains at least the polyurethane elastomer (d), which can improve the adhesiveness between the resin layer including the layer A and the topcoat layer. The layer B preferably contains the polyurethane elastomer (d) as the main component. In this case, the amount of the polyurethane elastomer (d) is preferably 50% by mass or more, more preferably 70% by mass or more, even more preferably 80% by mass or more, further preferably 90% by mass or more, of the resin component in the layer B. It is preferred that all resin component in the layer B be the polyurethane elastomer (d); otherwise, the remainder is preferably at least one of the polyamide elastomer (e) or the polyester elastomer (a) (the polyamide elastomer (e) and/or the polyester elastomer (a)).

Alternatively, the layer B may contain the polyamide elastomer (e) as the main component. For example, if the layer B contains the polyamide elastomer (e), the amount of the polyamide elastomer (e) may be 50% by mass or more, or 70% by mass or more, of the resin component. All resin component in the layer B may be the polyamide elastomer (e); otherwise, the remainder is preferably at least one of the polyurethane elastomer (d) or the polyester elastomer (a) (the polyurethane elastomer (d) and/or the polyester elastomer (a)), more preferably the polyurethane elastomer (d).

If the layer B is used as the outermost layer, the layer B preferably includes the hindered amine compound (b) and the compound (c). This can further improve the chemical resistance of the flexible tube. If the layer B is used as an inner layer or interlayer, it may be preferred not to include these compounds, for example, by taking into account adhesiveness to the outer layer, rather than chemical resistance. If the layer B is used as the outermost layer, preferred amounts of the hindered amine compound (b) and the compound (c), for example, are similar to those of the layer A.

Resin Composition for Covering Flexible Tube Substrate for Endoscope

The flexible tube according to the present invention is preferably produced using a resin composition for covering a flexible tube substrate for an endoscope according to the present invention. The resin composition for covering a flexible tube substrate for an endoscope according to the present invention includes a polyester elastomer (a), a hindered amine compound (b), and a compound (c).

Set of Resin Compositions for Covering Flexible Tube Substrate for Endoscope

A flexible tube according to the present invention in which the resin layer is composed of a plurality of layers is preferably produced using a set of resin compositions for covering a flexible tube substrate for an endoscope according to the present invention (a set of resin compositions for covering a flexible tube substrate for an endoscope is hereinafter also simply referred to as "set of resin compositions"). The set of resin compositions according to the present invention includes a resin composition (A) according to the present invention that includes a polyester elastomer (a), a hindered amine compound (b), and a compound (c) and a resin composition (B) that includes at least one of a polyester elastomer (a1), a polyurethane elastomer (d), or a polyamide elastomer (e) (a polyester elastomer (a1), a polyurethane elastomer (d), and/or a polyamide elastomer (e)). The resin compositions (A) and (B) are separately included in the set of resin compositions.

In the set of resin compositions according to the present invention, the polyester elastomer (a) and the polyester elastomer (a1) may be the same or different.

The resin composition (A) is used to form the layer A of the resin layer of the flexible tube according to the present invention. The resin composition (B), on the other hand, is used to form a layer other than the layer A of the resin layer. The resin composition (B) may include any component present in the resin composition (A) as long as the advantages of the present invention are not impaired.

Preferred ratios of the amount of the polyester elastomer (a), the amount of the hindered amine compound (b), and the amount of the compound (c) in the resin composition (A), for example, are the same as those of the layer A.

The flexible tube according to the present invention preferably includes a resin layer having a two-layer structure composed of one inner layer and one outer layer. In this case, the inner layer is composed of the layer B of the resin layer, whereas the outer layer is composed of the layer A of the resin layer. Preferred formulations for the resin layer are as follows.

If the adhesiveness between the inner layer and the outer layer is prioritized

|  |  | Elastomer | Additive |
|---|---|---|---|
| Inner layer | Layer B | PU (PE, PA) |  |
| Outer layer | Layer A | PE (PU, PA) | HA, Ad |

|  |  | Elastomer | Additive |
|---|---|---|---|
| Inner layer | Layer B | PU (PE, PA) | HA, Ad |
| Outer layer | Layer A | PE (PU, PA) | HA, Ad |

PE: polyester elastomer (a)
PU: polyurethane elastomer (d)
PA: polyamide elastomer (e)
HA: hindered amine compound (b)
Ad: compound (c) represented by any of formulae (TS-I) to (TS-III)

The constituents in parentheses are optional.

Physical Properties

To improve the chemical resistance, the molecular weights of the elastomers applied are preferably, but not limited to, 10,000 to 1,000,000, more preferably 20,000 to 500,000, particularly preferably 30,000 to 300,000.

In the present invention, the molecular weight of an elastomer refers to the weight average molecular weight unless otherwise specified. The weight average molecular weight can be determined by GPC as the molecular weight based on polystyrene. An HLC-8220 GPC apparatus (trade name, available from Tosoh Corporation) is used. The eluants used are chloroform for polyester elastomers, N-methyl-2-pyrrolidone (NMP) for polyurethane elastomers, and m-cresol/chloroform (available from Shonan Wako Pure Chemical Co., Ltd.) for polyamide elastomers. The columns used are G3000HXL and G2000HXL (trade names, available from Tosoh Corporation). The temperature is 23° C. The flow rate is 1 mL/min. RI detection is employed.

It is preferred to suitably set the physical properties of the layer B (preferably the inner layer). For example, the layer B preferably has an A hardness (JIS-K7215) of 40 or more, more preferably 50 or more, particularly preferably 60 or more. The upper limit is preferably 98 or less, more preferably 95 or less, particularly preferably 90 or less.

The layer B preferably has a storage modulus E' of 1 MPa or more, more preferably 2 MPa or more, particularly preferably 3 MPa or more. The upper limit is preferably 150 MPa or less, more preferably 100 MPa or less, particularly preferably 50 MPa or less. The layer B preferably has a loss modulus E" of 0.1 MPa or more, more preferably 0.3 MPa or more, particularly preferably 0.5 MPa or more. The upper limit is preferably 20 MPa or less, more preferably 10 MPa or less, particularly preferably 5 MPa or less. The layer B preferably has a loss tangent of 0.01 or more, more preferably 0.03 or more, particularly preferably 0.05 or more. The upper limit is preferably 1 or less, more preferably 0.5 or less, particularly preferably 0.3 or less.

As used herein, the viscoelasticity parameters are measured at 25° C. unless otherwise specified. The measurement procedure follows JIS-K7244-4.

It is preferred to suitably set the physical properties of the layer A of the resin layer. For example, the layer A preferably has a D hardness (JIS-K7215) of 40 or more, more preferably 45 or more, particularly preferably 55 or more. The upper limit is preferably 90 or less, particularly preferably 85 or less.

The layer A of the resin layer preferably has a storage modulus E' of 1 MPa or more, more preferably 5 MPa or more, particularly preferably 10 MPa or more. The upper limit is preferably 1 GPa or less, more preferably 500 MPa or less, particularly preferably 300 MPa or less. The layer A of the resin layer preferably has a loss modulus E" of 0.1 MPa or more, more preferably 0.5 MPa or more, particularly preferably 1 MPa or more. The upper limit is preferably 100 MPa or less, more preferably 50 MPa or less, particularly preferably 30 MPa or less. The layer A of the resin layer preferably has a loss tangent of 0.01 or more, more preferably 0.03 or more, particularly preferably 0.05 or more. The upper limit is preferably 1 or less, more preferably 0.5 or less, particularly preferably 0.3 or less.

The layer B preferably has a modulus at 100% elongation of 0.5 MPa or more, more preferably 1.0 MPa or more, particularly preferably 1.5 MPa or more. The upper limit is preferably 20 MPa or less, more preferably 15 MPa or less, particularly preferably 10 MPa or less.

The layer A of the resin layer preferably has a modulus at 100% elongation of 1.0 MPa or more, more preferably 1.5 MPa or more, particularly preferably 2.0 MPa or more. The upper limit is preferably 80 MPa or less, more preferably 70 MPa or less, particularly preferably 65 MPa or less.

As used herein, the modulus is measured at 25° C. unless otherwise specified. The measurement procedure follows JIS-K7311.

The resin layer is preferably soluble in 1,1,1,3,3,3-hexafluoro-2-propanol (specific solvent). "Soluble in the specific solvent" means that the resin layer exhibits a degree of solubility of 5% by mass or more at 20° C. Thus, the technical significance of "soluble in the specific solvent" is that the resin has no three-dimensional (crosslinked) structure, which is preferred because the use of such a resin layer provides good flexibility for a flexible tube for an endoscopic medical device.

The elastomer forming the resin layer is preferably not substantially crosslinked. Here, "not substantially crosslinked" not only means that the resin is not crosslinked, but also means that the resin has no branched structure within the detection limit of, for example, NMR.

It is preferred that the elastomer forming the resin layer (particularly the second layer or the outer layer) according to this embodiment be not substantially crosslinked because the use of such a resin layer provides good flexibility and bending durability for a flexible tube for an endoscopic medical device.

Topcoat Layer

The topcoat layer (coat layer) 16 is applied to the flexible tube according to this embodiment. Examples of materials the can be applied to the topcoat layer include, but not limited to, urethane coatings, acrylic coatings, fluorinated coatings, silicone coatings, epoxy coatings, and polyester coatings. To achieve high adhesiveness between the resin layer and the topcoat layer and good chemical resistance, which are advantages of this embodiment, urethane coatings, acrylic coatings, and fluorinated coatings are preferred. The topcoat layer may be formed by common processes. One example process involves dissolving the coating component in a predetermined solvent, optionally adding a curing agent to the solution, and hardening the solution. The hardening treatment may be performed, for example, by heating to 100° C. to 200° C.

In this embodiment, the topcoat layer is primarily used to protect and add a gloss to the surface of the flexible tube and to impart smoothness and chemical resistance. Thus, a topcoat layer with high elasticity, high surface smoothness, and good chemical resistance is preferred. The topcoat layer alone preferably has a storage modulus E' of 1 MPa or more, more preferably 5 MPa or more, particularly preferably 10 MPa or more. The upper limit is preferably 1 GPa or less, more preferably 500 MPa or less, particularly preferably 300 MPa or less. If the storage modulus E' is higher than or equal to the lower limit, the topcoat layer can provide a surface protection function. If the storage modulus E' is lower than or equal to the upper limit, the resulting flexible tube can maintain its flexibility.

Although a two-layer molded resin layer composed of a soft resin layer (layer B) as an inner layer and a hard resin layer (layer A) as an outer layer is formed in the foregoing embodiment, the hard resin layer may be disposed as the inner layer, and the soft resin layer may be disposed as the outer layer. Although a skin layer having a two-layer configuration has been described by way of example in the foregoing embodiment, the skin layer may have a multilayer configuration including two or more layers. The two layers need not be in contact with each other, but may be separated by another functional layer.

Although an electronic endoscope for observation of an image of the condition of a subject captured using an imaging device has been described by way of example in the foregoing embodiment, the present invention is not limited thereto, but may also be applied to an endoscope for observation of the condition of a subject using an optical image guide.

The flexible tube according to the present invention is not limited to endoscope applications, but can also be applied to a wide variety of endoscopic medical devices. For example, the flexible tube according to the present invention can be applied to an endoscope equipped with a clip or wire at the distal end thereof or to a device equipped with a basket or brush and provides its superior effect. Endoscopic medical devices are meant to include a wide variety of flexible medical and diagnostic devices for introduction and use in a body, including medical devices having an endoscope as a basic structure, as described above, and remotely operated medical devices.

Examples

The present invention will now be described in more detail with reference to the following examples, although these examples should not be construed as limiting the invention.

Examples and Comparative Examples

Resin compositions (resin mixtures for outer and inner layers) having the formulations shown in Table 1 below (in parts by mass) were prepared and were melt-kneaded in a twin-screw kneader available from Technovel Corporation (product name: KZW15-30MG) at a barrel set temperature of 220° C. and a screw rotational speed of 100 rpm. The ejected molten resin strand was cooled in a water bath and was pelletized with a pelletizer to form pelletized samples.

Figure 3:
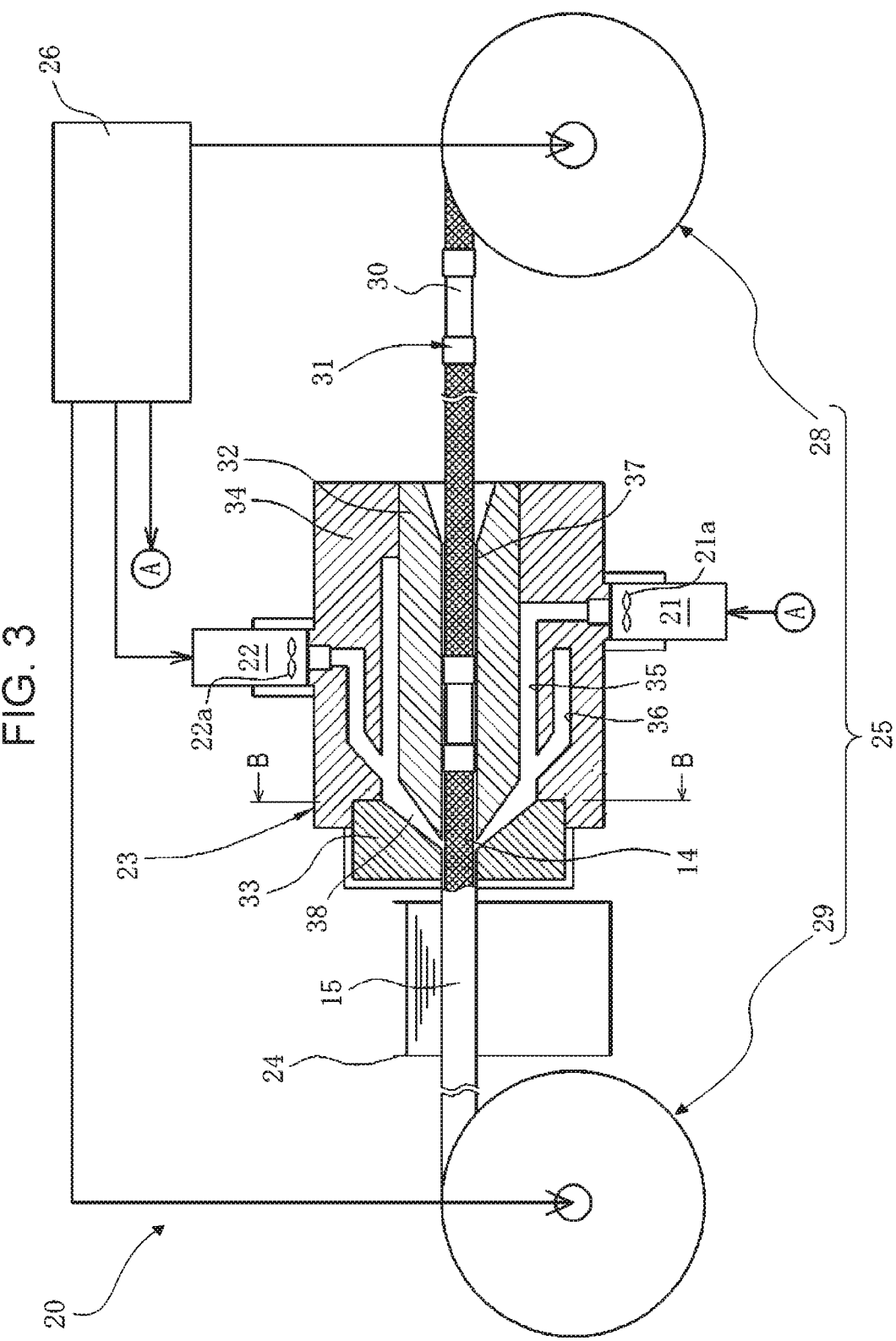
FIG. 3 is a block diagram schematically illustrating the configuration of an apparatus for manufacturing the flexible tube for an endoscope.
Figure 4:
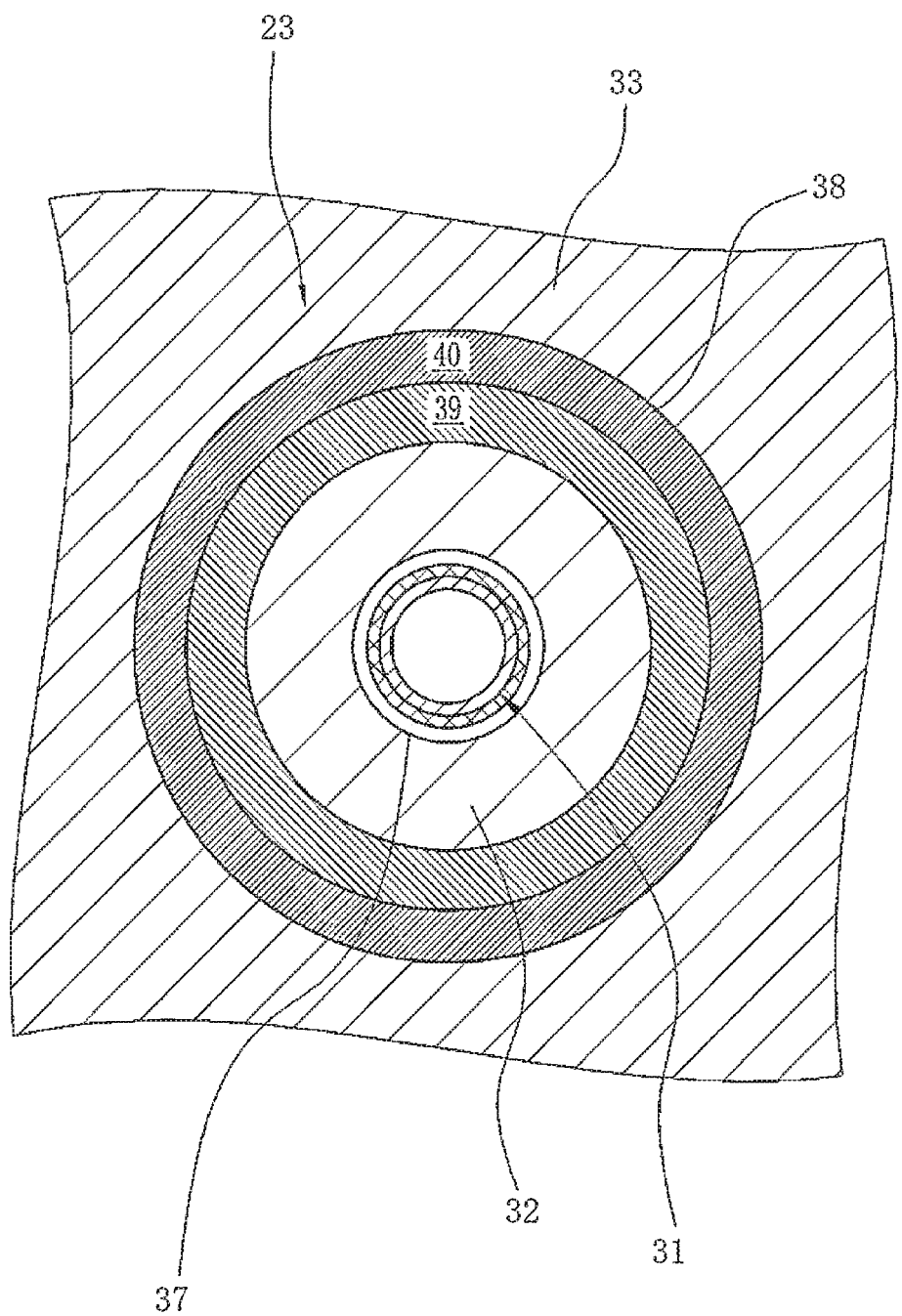
FIG. 4 is a sectional view taken along line B-B of FIG. 3.

The resulting pelletized samples were introduced into the continuous molding machine shown in FIGS. 3 and 4 to produce flexible tubes for endoscopes. Specifically, flexible tube substrates having a diameter of 5.0 mm and a length of 120 cm were covered with the resin mixtures (compositions) for the inner layer and then with the resin mixtures (compositions) for the outer layer in Table 1 below. The resin layer had a thickness of 0.3 mm. The inner-to-outer-layer ratios at the distal and proximal ends were as shown in Table 2 below. For flexible tubes having no inner layer, the inner-to-outer-layer ratio is shown as inner layer:outer layer=0:100. The resulting flexible tubes were subjected to the following tests. The results are summarized in Table 2.

Appearance Visual Inspection Test

The resin was removed from each flexible tube and was cut to a size of 1 cm×10 cm to obtain a test specimen. The test specimen was immersed in a 0.3% aqueous peracetic acid solution at 50° C. for 150 hours. After the surface of the test specimen was thoroughly washed with water and was then dried at 23° C. and 50% RH for 24 hours, the surface of the test specimen was visually observed and was rated for surface whitening and cracking on the following scale, where "B" or higher is satisfactory. The results are summarized in Table 2.

Rating Scale

A: The surface exhibited no whitening or cracking.

B: The surface exhibited slight whitening or cracking in 1 to less than 5 places.

C: The surface exhibited slight whitening or cracking in 5 to 20 places.

D: The surface exhibited noticeable whitening or cracking.

Peracetic Acid Resistance

The resin was removed from each flexible tube and was cut to a size of 1 cm×10 cm to obtain a test specimen. The test specimen was immersed in a 0.3% aqueous peracetic acid solution at 50° C. for 150 hours. After the surface of the test specimen was thoroughly washed with water and was then dried at 23° C. and 50% RH (relative humidity) for 24 hours, the test specimen was subjected to a tensile test at elongations of 50%, 100%, and 200% (an elongation of 100% means stretching to twice the original length) with a TENSILON RTF-1210 universal material testing machine (trade name, available from A&D Company, Limited). The test specimen was rated on the following scale, where "B" or higher is satisfactory. The results are summarized in Table 2.

Rating Scale

A: The test specimen was not broken after a tensile test at an elongation of 200%.

B: The test specimen was not broken after a tensile test at an elongation of 100%, but was broken after a tensile test at an elongation of 200%.

C: The test specimen was not broken after a tensile test at an elongation of 50%, but was broken after a tensile test at an elongation of 100%.

D: The test specimen was broken after a tensile test at an elongation of 50%.

Adhesiveness Evaluation

The resulting resin mixtures were used to form sheet-shaped articles. The results are summarized in Table 2.

Sheet Formation Conditions

Each resin composition for the outer layer was heated to 220° C. and was pressed at 10 MPa for 30 seconds using a MINI TEST PRESS (available from Toyo Seiki Seisaku-sho, Ltd.) to form a 0.5 mm thick, 10 cm square sheet.

Topcoat Layer Formation Conditions

The resulting sheet was coated with a topcoat layer under the following conditions.

The material used for the topcoat layer was Obbligato SS0068 (trade name, available from AGC COAT-TECH Co., Ltd.), serving as a base, with a curing agent (available from AGC COAT-TECH Co., Ltd.). This material was applied to the sheet formed as above with a 100 μm thick doctor blade. The coated sample was dried at room temperature (25° C.) and was further dried at 80° C. for 10 hours to form a resin sheet with a topcoat layer. The topcoat layer had a thickness of 0.02 mm.

Peracetic Acid Immersion Test on Resin Sheet with Topcoat Layer

The resulting resin sheet with a topcoat layer was immersed in a 0.3% aqueous peracetic acid solution at 50° C. for 50 hours. After the surface was washed with water and was then dried at 23° C. and 50% RH for 24 hours, the following adhesiveness evaluation was performed.

Adhesiveness Evaluation

A polyester tape (available from 3M Company, model No. 850, length: 5 cm, width: 1.5 cm) was attached to the topcoat layer side of the resulting resin sheet with a topcoat layer that had been subjected to the peracetic acid immersion test. The polyester tape was then removed to determine whether the topcoat layer peeled from the resin sheet. On the following rating scale, "B" or higher is satisfactory.

Rating Scale

A: The test was performed ten times, and the topcoat layer did not peel at all.

B: The test was performed ten times, and the topcoat layer peeled one to three out of ten times.

C: The test was performed ten times, and the topcoat layer peeled four to nine out of ten times.

D: The test was performed ten times, and the topcoat layer peeled every time.

TABLE 1

| Resin mixture | | A-1 | A-2 | A-3 | A-4 | A-5 | A-6 | A-7 | A-8 | A-9 | A-10 | A-11 | A-12 | A-13 |
|---|---|---|---|---|---|---|---|---|---|---|---|---|---|---|
| | | \multicolumn{13}{c}{Resin for outer layer} |
| Elastomer | PE-1 | 100 | | | | | | 100 | 100 | 80 | | | | 100 |
| | PE-2 | | 100 | | | 100 | 100 | | | | 90 | 85 | 90 | |
| | PE-3 | | | 100 | | | | | | | | | | |
| | PE-4 | | | | 100 | | | | | | | | | |
| | PU-1 | | | | | | | | | 20 | | | | |
| | PU-2 | | | | | | | | | | 10 | | | |
| | PA-1 | | | | | | | | | | | 15 | | |
| | PA-2 | | | | | | | | | | | | 10 | |
| Hindered amine compound | HALS-1 | | | | 1 | | | | | | | | | |
| | HALS-2 | 1 | | | | | | | 0.5 | 1 | | 1 | 1 | 0.1 |
| | HALS-3 | | 1 | | | | | | | | | | | |
| | HALS-4 | | | | | | | 2 | | | | | | |
| | HALS-5 | | | 1 | | 1 | 1 | | | | 1 | | | |
| Other additives | HA-1 | 0.5 | | | | 0.25 | | 0.15 | 0.0375 | | 0.5 | | | |
| | AM-1 | | 0.5 | | | 0.25 | | | | | 0.5 | 0.25 | 0.05 | 0.025 |
| | L-1 | | | 0.5 | | | 0.25 | | | | | | | |
| | AS-1 | | | | 0.5 | | 0.25 | | | | | | | |
| | BZ-1 | | | | | | | | | | | | | |
| Amount of hindered amine compound added | | 1 | 1 | 1 | 1 | 1 | 1 | 2 | 0.5 | 1 | 1 | 1 | 1 | 0.1 |
| Amount of other additives added | | 0.5 | 0.5 | 0.5 | 0.5 | 0.5 | 0.5 | 0.15 | 0.0375 | 0.5 | 0.5 | 0.25 | 0.05 | 0.025 |
| Ratio of amounts added (amount of hindered amine compound added/ amount of other additives added) | | 2.0 | 2.0 | 2.0 | 2.0 | 2.0 | 2.0 | 13.3 | 13.3 | 2 | 2 | 4 | 20 | 4 |

| Resin mixture | | A-14 | A-15 | A-16 | A-17 | C-1 | C-2 | C-3 | C-4 | C-5 | B-1 | B-2 |
|---|---|---|---|---|---|---|---|---|---|---|---|---|
| | | \multicolumn{9}{c}{Resin for outer layer} | \multicolumn{2}{c}{Resin for inner layer} |
| Elastomer | PE-1 | 80 | | | 60 | 100 | 100 | 100 | 100 | | | |
| | PE-2 | | 80 | | | | | | | | | 10 |
| | PE-3 | | | 100 | | | | | | | | |
| | PE-4 | | | | | | | | | | | |
| | PU-1 | 20 | | | | | | | | 100 | 100 | 90 |
| | PU-2 | | | | 40 | | | | | | | |
| | PA-1 | | 20 | | | | | | | | | |
| | PA-2 | | | | | | | | | | | |
| Hindered amine compound | HALS-1 | | | | 1 | | | | 2 | | | |
| | HALS-2 | | | | | 1 | 1 | | | 1 | 0.5 | 0.5 |
| | HALS-3 | | 0.1 | | | | | | | | | |
| | HALS-4 | 2 | | | | | | | | | | |
| | HALS-5 | | | 0.2 | | | | | | | | |
| Other additives | HA-1 | | | | | | | | | 0.5 | | |
| | AM-1 | 0.04 | 2 | | | | | | | | 0.125 | 0.125 |
| | L-1 | | | 2 | | | | | | | | |
| | AS-1 | | | | 0.5 | | | | | | | |
| | BZ-1 | | | | | | | 0.5 | 0.5 | | | |
| Amount of hindered amine compound added | | 2 | 0.1 | 0.2 | 1 | 0 | 1 | 1 | 2 | 1 | 0.5 | 0.5 |
| Amount of other additives added | | 0.04 | 2 | 2 | 0.5 | 0 | 0 | 0.5 | 0.5 | 0.5 | 0.125 | 0.125 |
| Ratio of amounts added (amount of hindered amine compound added/ amount of other additives added) | | 50 | 0.05 | 0.1 | 2 | | | 2 | 4 | 2 | 4 | 4 |

Description of Terms in Tables

Elastomers (1) Polyester elastomers (the values in parentheses are D hardnesses (JIS-K7215))

PE-1: Hytrel 7247 (D72), trade name, available from DuPont-Toray Co., Ltd. (weight average molecular weight: 81,000, modulus at 100% elongation: 60.7 MPa)

PE-2: Hytrel 6347 (D63), trade name, available from DuPont-Toray Co., Ltd. (weight average molecular weight: 82,000, modulus at 100% elongation: 50.1 MPa)

PE-3: Arnitel UM622 (D62), trade name, available from DSM Japan Engineering Plastics K.K. (weight average molecular weight: 116,000, modulus at 100% elongation: 45.0 MPa)

PE-4: Pelprene E450B (D78), trade name, available from Toyobo Co., Ltd. (weight average molecular weight: 121,000, modulus at 100% elongation: 70.3 MPa)

(2) Polyurethane elastomers (the values in parentheses are A hardnesses (JIS-K7215))

PU-1: Miractran E585 (A85), trade name, available from Nippon Miractran Co., Ltd. (weight average molecular weight: 99,000, modulus at 100% elongation: 6.4 MPa)

PU-2: Elastollan ET 1080 (A80), trade name, available from BASF SE (weight average molecular weight: 124,000, modulus at 100% elongation: 4.0 MPa)

(3) Polyamide elastomers (the values in parentheses are A hardnesses (JIS-K7215))

PA-1: Pebax 2533 (A75), trade name, available from Arkema Inc. (weight average molecular weight: 208,000, modulus at 100% elongation: 4.4 MPa)

PA-2: Pebax 3533 (A83), trade name, available from Arkema Inc. (weight average molecular weight: 171,000, modulus at 100% elongation: 6.0 MPa)

Hindered Amine Compounds

HALS-1: ADK STAB LA-63P (trade name), available from Adeka Corporation

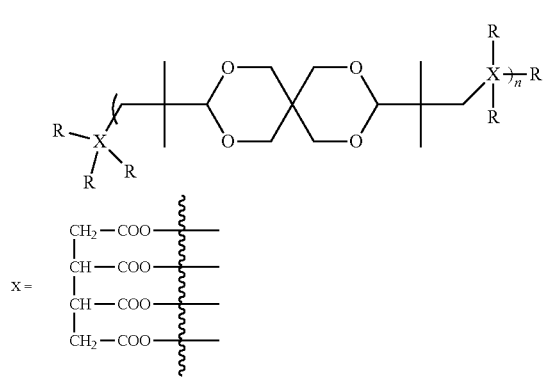

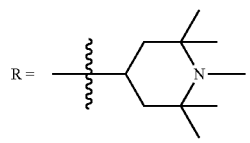

where the wavy lines represent a point of attachment, which also applies to the following formulae; and n represents 1 or 2.

HALS-2: Chimassorb 944FDL (trade name), available from BASF SE

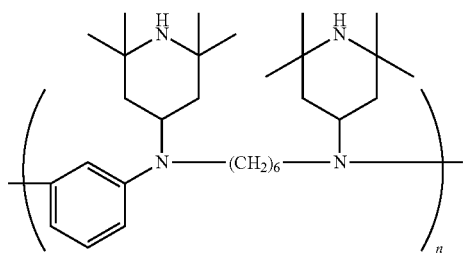

where n represents an integer of 2 to 5.

HALS-3: Tinuvin 765 (trade name), available from BASF SE

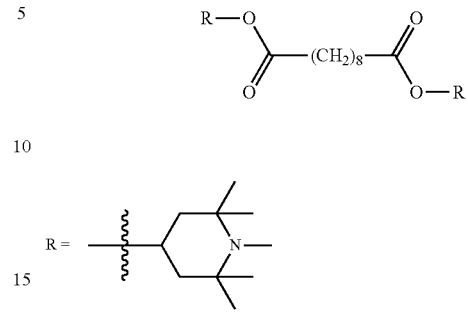

HALS-4: Flamestab NOR 116 (trade name), available from BASF SE

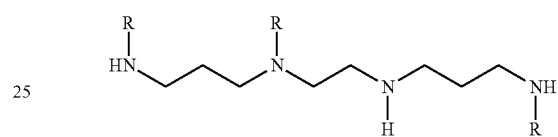

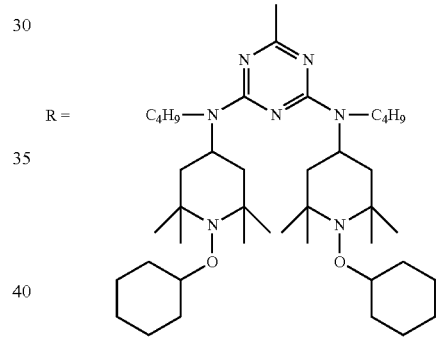

HALS-5: Chimassorb 2020FDL (trade name), available from BASF SE

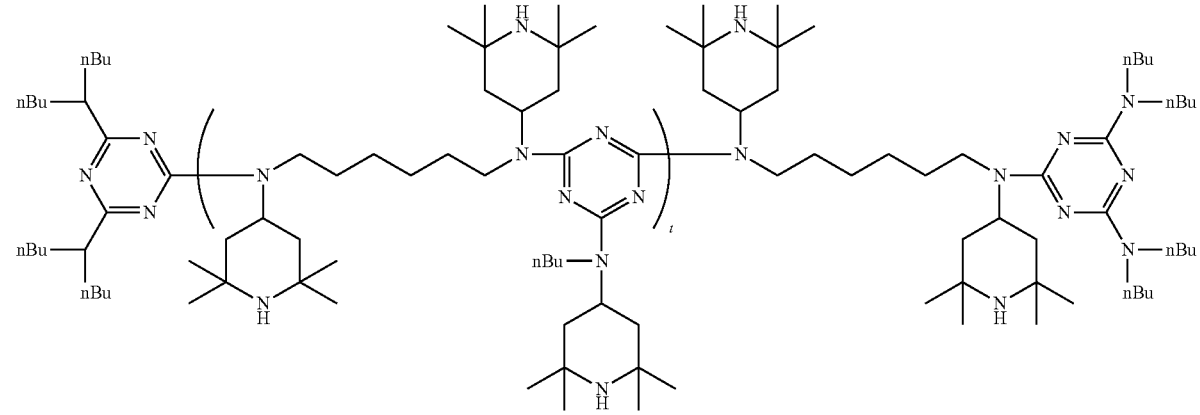

where t represents an integer of 2 to 4, and nBu represents a n-butyl group.

Other Additives

HA-1: Irgastab FS-042 (trade name), available from Sigma-Aldrich Co.

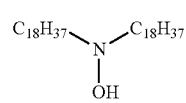

AM-1: lauryldiethanolamide (trade name), available from Fujifilm Wako Pure Chemical Corporation

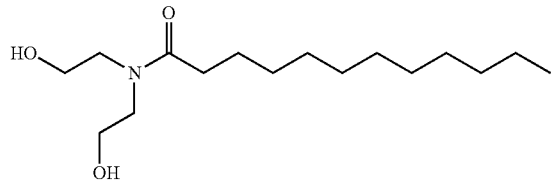 [SMILES: CCCCCCCCCCCC(=O)N(CCO)CCO]

L-1: Irganox HP-136 (trade name), available from BASF SE

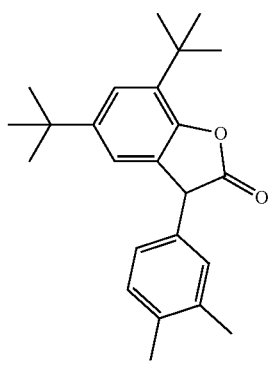 [SMILES: Cc1ccc(C2C(=O)Oc3c2cc(C(C)(C)C)cc3C(C)(C)C)cc1C]

AS-1: ascorbic acid, available from Fujifilm Wako Pure Chemical Corporation

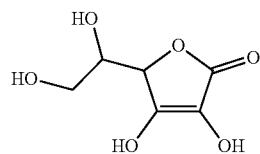

BZ-1: benzotriazole

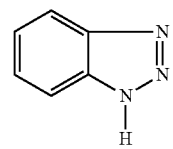

TABLE 2

| | Example 1 | Example 2 | Example 3 | Example 4 | Example 5 | Example 6 | Example 7 | Example 8 | Example 9 | Example 10 | Example 11 | Example 12 |
|---|---|---|---|---|---|---|---|---|---|---|---|---|
| Outer layer | A-1 | A-2 | A-3 | A-4 | A-5 | A-6 | A-7 | A-8 | A-9 | A-10 | A-11 | A-12 |
| Inner layer | None | None | None | None | None | None | None | None | None | None | None | None |
| Inner layer:outer layer (proximal end) | 0:100 | 0:100 | 0:100 | 0:100 | 0:100 | 0:100 | 0:100 | 0:100 | 0:100 | 0:100 | 0:100 | 0:100 |
| Inner layer:outer layer (distal end) | 0:100 | 0:100 | 0:100 | 0:100 | 0:100 | 0:100 | 0:100 | 0:100 | 0:100 | 0:100 | 0:100 | 0:100 |
| Appearance | A | A | A | A | A | A | A | B | A | A | A | A |
| Tensile test | A | A | A | A | A | A | A | B | A | A | A | A |
| Adhesiveness | B | B | B | B | B | B | B | B | A | A | A | A |

| | Example 13 | Example 14 | Example 15 | Example 16 | Example 17 | Example 18 | Example 19 | Comparative Example 1 | Comparative Example 2 | Comparative Example 3 | Comparative Example 4 | Comparative Example 5 |
|---|---|---|---|---|---|---|---|---|---|---|---|---|
| Outer layer | A-13 | A-1 | A-2 | A-14 | A-15 | A-16 | A-17 | C-1 | C-2 | C-3 | C-4 | C-5 |
| Inner layer | None | B-1 | B-2 | None | None | None | None | None | None | None | None | None |
| Inner layer:outer layer (proximal end) | 0:100 | 20:80 | 20:80 | 0:100 | 0:100 | 0:100 | 0:100 | 0:100 | 0:100 | 0:100 | 0:100 | 0:100 |
| Inner layer:outer layer (distal end) | 0:100 | 80:20 | 80:20 | 0:100 | 0:100 | 0:100 | 0:100 | 0:100 | 0:100 | 0:100 | 0:100 | 0:100 |
| Appearance | B | A | A | B | A | A | B | D | D | D | D | D |
| Tensile test | B | A | A | A | B | B | A | C | A | A | A | B |
| Adhesiveness | B | A | A | A | A | B | A | D | D | D | D | B |

As can be seen from Table 2, it was found that the flexible tubes having resin layers that did not meet the requirements of the present invention had low chemical resistance and also exhibited at least poor appearance after disinfection. Comparative Example 5 exhibited poor appearance because the use of a polyurethane elastomer results in the surface becoming dull even after slight degradation.

In contrast, it was found that, after disinfection, the flexible tubes according to the present invention exhibited sufficiently reduced degradation in appearance, had good tensile strength, and had a higher adhesiveness between the topcoat layer and the resin layer.

While the present invention has been described in connection with embodiments thereof, we do not intend to limit our invention in any detail of the description unless otherwise specified. Rather, the invention should be broadly construed without departing from the spirit and scope of the invention as defined by the appended claims.

2 electronic endoscope (endoscope)
3 insertion section
3a flexible tube
3b angle portion
3c tip portion
5 main-body operating section
6 universal cord
11 spiral tube
11a metal strip
12 tubular net
13 cap
14 flexible tube substrate
14a distal side
14b proximal side
15 resin layer
16 coat layer
17 inner layer
18 outer layer
X angle portion 3b side (soft)
Y main-body operating section 5 side (hard)
20 continuous molding machine (manufacturing apparatus)
21, 22 extrusion unit
21a screw
22a screw
23 head unit
24 cooling unit
25 transport unit
26 control unit
28 feed drum
29 take-up drum
30 joint member
31 continuous flexible tube substrate
32 nipple
33 die
34 support
35, 36 gate
37 molding passage
38 resin passage
39 soft resin
40 hard resin

What is claimed is:

1. A flexible tube for an endoscope, comprising a flexible tube substrate, for an endoscope, that is flexible and tubular and a resin layer covering the flexible tube substrate for an endoscope, wherein the resin layer includes one or more layers, the layers including a layer A including a polyester elastomer (a) as a resin component, a hindered amine compound (b), and a compound (c) represented by any of formulae (TS-I) to (TS-III):

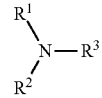

(TS-I)

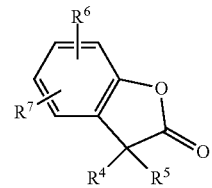

(TS-II)

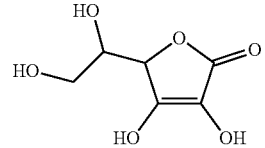 [SMILES: O=C1OC(C(O)CO)C(O)=C1O]

(TS-III)

wherein in formula (TS-I), $R^1$ and $R^2$ represent a hydrogen atom, an aliphatic group, an acyl group, an aliphatic oxycarbonyl group, an aromatic oxycarbonyl group, an aliphatic sulfonyl group, or an aromatic sulfonyl group; $R^3$ represents an unsubstituted aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, a hydroxy group or an aliphatic group to which a halogen atom, an aryl group, a heterocyclic group, a cyano group, a hydroxy group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an unsubstituted amino group, an alkylamino group, an anilino group, a formylamino group, an unsubstituted alkylcarbonylamino group, an arylcarbonylamino group, an aminocarbonylamino group, an alkoxycarbonylamino group, an aryloxycarbonylamino group, a sulfamoylamino group, an alkylsulfonylamino group, an arylsulfonylamino group, a sulfanyl group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imide group, a phosphino group, a phosphinyl group, a phosphinyloxy group, a phosphinylamino group, or a silyl group bind; and $R^1$ and $R^2$, $R^2$ and $R^3$, or $R^1$ and $R^3$ may be attached to each other to form a 5- to 7-membered ring, but do not form a 2,2,6,6-tetraalkylpiperidine skeleton; provided that $R^1$ and $R^2$ are not simultaneously hydrogen atoms and have a total of 7 or more carbon atoms, and in formula (TS-II), $R^4$ to $R^7$ represent a hydrogen atom, an alkyl group having 1 to 20 carbon atoms, or an aryl group having 6 to 15 carbon atoms.

2. The flexible tube for an endoscope according to claim 1, wherein an amount of the polyester elastomer (a) is 50% by mass or more of the resin component in the layer A.

3. The flexible tube for an endoscope according to claim 1, wherein the layers include the layer A and a layer B including a polyurethane elastomer (d).

4. The flexible tube for an endoscope according to claim 1, wherein the layer A further contains, as the resin component, at least one of a polyurethane elastomer (d) or a polyamide elastomer (e).

5. The flexible tube for an endoscope according to claim 1, wherein an amount of the compound (c) is 0.01 to 5 parts by mass based on 100 parts by mass of the resin component in the layer A.

6. The flexible tube for an endoscope according to claim 1, wherein an amount of the hindered amine compound (b) is 0.01 to 5 parts by mass based on 100 parts by mass of the resin component in the layer A.

7. The flexible tube for an endoscope according to claim 1, wherein a ratio of an amount of the hindered amine compound (b) to an amount of the compound (c) is 1:50 to 50:1 by mass.

8. The flexible tube for an endoscope according to claim 1, wherein the hindered amine compound (b) has a structural moiety represented by general formula (1):

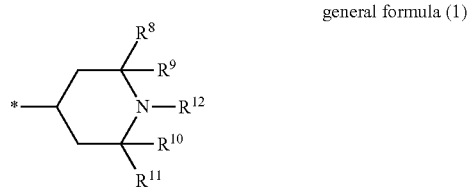

general formula (1)

wherein $R^8$ to $R^{11}$ represent a hydrogen atom or an alkyl group having 1 to 12 carbon atoms; $R^{12}$ represents a hydrogen atom, an alkyl group having 1 to 18 carbon atoms, or $-OR^{13}$, wherein $R^{13}$ represents a hydrogen atom or an alkyl group having 1 to 20 carbon atoms; and * represents a point of attachment.

9. The flexible tube for an endoscope according to claim 1, wherein the hindered amine compound (b) is a compound represented by general formula (1-1) or a compound having a component represented by general formula (1-2):

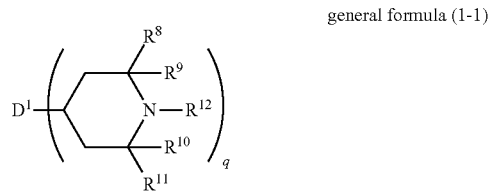

general formula (1-1)

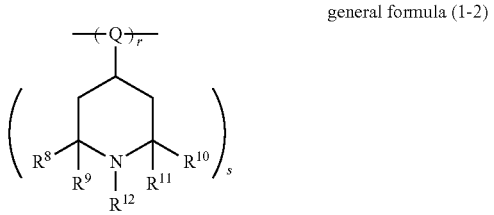

general formula (1-2)

wherein $R^8$ to $R^{12}$ have the same meanings as $R^8$ to $R^{12}$, respectively, in general formula (1); q represents an integer of 2 or more; $D^1$ represents a q-valent linking group; r represents a positive integer; Q represents an s+2-valent linking group; and s represents 1 or 2.

10. The flexible tube for an endoscope according to claim 1, wherein the compound represented by formula (TS-I) is a compound represented by formula (TS-IA) or (TS-IB):

(TS-IA)

(TS-IB)

wherein in formula (TS-IA), $R^1$ and $R^2$ have the same meanings as $R^1$ and $R^2$, respectively, in formula (TS-I); and $R^{b1}$ represents a hydrogen atom, an aliphatic group, an acyl group, an aliphatic oxycarbonyl group, or an aromatic oxycarbonyl group, and in formula (TS-IB), $R^{b2}$ and $R^{b3}$ represent an aliphatic group or an acyl group; and RM represents an unsubstituted aliphatic group or an aliphatic group to which a halogen atom, an aryl group, a heterocyclic group, a cyano group, a hydroxy group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an unsubstituted amino group, an alkylamino group, an anilino group, a formylamino group, an unsubstituted alkylcarbonylamino group, an arylcarbonylamino group, an aminocarbonylamino group, an alkoxycarbonylamino group, an aryloxycarbonylamino group, a sulfamoylamino group, an alkylsulfonylamino group, an arylsulfonylamino group, a sulfanyl group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imide group, a phosphino group, a phosphinyl group, a phosphinyloxy group, a phosphinylamino group, or a silyl group bind.

11. The flexible tube for an endoscope according to claim 1, further comprising a topcoat layer.

12. An endoscopic medical device comprising the flexible tube for an endoscope according to claim 1.

13. A resin composition for covering a flexible tube substrate for an endoscope, comprising a polyester elastomer (a), a hindered amine compound (b), and a compound (c) represented by any of formulae (TS-I) to (TS-III):

(TS-I)

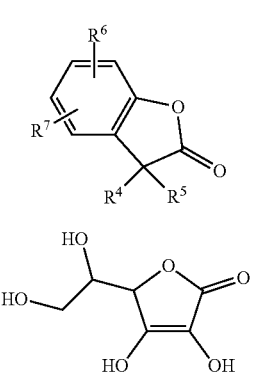

(TS-II)

(TS-III)

wherein
in formula (TS-I), $R^1$ and $R^2$ represent a hydrogen atom, an aliphatic group, an acyl group, an aliphatic oxycarbonyl group, an aromatic oxycarbonyl group, an aliphatic sulfonyl group, or an aromatic sulfonyl group; $R^3$ represents an unsubstituted aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, a hydroxy group or an aliphatic group to which a halogen atom, an aryl group, a heterocyclic group, a cyano group, a hydroxy group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an unsubstituted amino group, an alkylamino group, an anilino group, a formylamino group, an unsubstituted alkylcarbonylamino group, an arylcarbonylamino group, an aminocarbonylamino group, an alkoxycarbonylamino group, an aryloxycarbonylamino group, a sulfamoylamino group, an alkylsulfonylamino group, an arylsulfonylamino group, a sulfanyl group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imide group, a phosphino group, a phosphinyl group, a phosphinyloxy group, a phosphinylamino group, or a silyl group bind; and $R^1$ and $R^2$, $R^2$ and $R^3$, or $R^1$ and $R^3$ may be attached to each other to form a 5- to 7-membered ring, but do not form a 2,2,6,6-tetraalkylpiperidine skeleton; provided that $R^1$ and $R^2$ are not simultaneously hydrogen atoms and have a total of 7 or more carbon atoms, and in formula (TS-II), $R^4$ to $R^7$ represent a hydrogen atom, an alkyl group having 1 to 20 carbon atoms, or an aryl group having 6 to 15 carbon atoms.

14. The resin composition for covering a flexible tube substrate for an endoscope according to claim 13, wherein a ratio of an amount of the hindered amine compound (b) to an amount of the compound (c) is 1:50 to 50:1 by mass.

15. A set of resin compositions for covering a flexible tube substrate for an endoscope, comprising:
a resin composition (A) including a polyester elastomer (a), a hindered amine compound (b), and a compound (c); and a resin composition (B) including at least one of a polyester elastomer (a1), a polyurethane elastomer (d), or a polyamide elastomer (e),
wherein the compound (c) is represented by any of formulae (TS-I) to (TS-III):

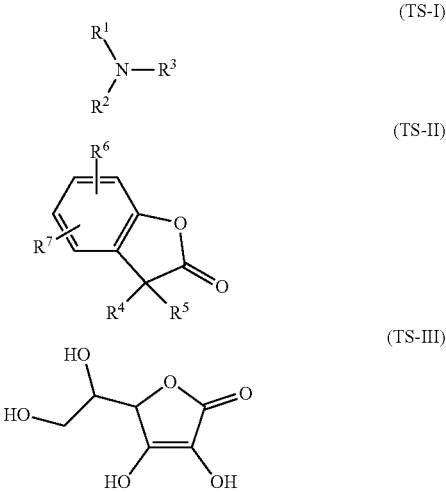

wherein
in formula (TS-I), $R^1$ and $R^2$ represent a hydrogen atom, an aliphatic group, an acyl group, an aliphatic oxycarbonyl group, an aromatic oxycarbonyl group, an aliphatic sulfonyl group, or an aromatic sulfonyl group; $R^3$ represents an unsubstituted aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, a hydroxy group or an aliphatic group to which a halogen atom, an aryl group, a heterocyclic group, a cyano group, a hydroxy group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an unsubstituted amino group, an alkylamino group, an anilino group, a formylamino group, an unsubstituted alkylcarbonylamino group, an arylcarbonylamino group, an aminocarbonylamino group, an alkoxycarbonylamino group, an aryloxycarbonylamino group, a sulfamoylamino group, an alkylsulfonylamino group, an arylsulfonylamino group, a sulfanyl group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imide group, a phosphino group, a phosphinyl group, a phosphinyloxy group, a phosphinylamino group, or a silyl group bind; and $R^1$ and $R^2$, $R^2$ and $R^3$, or $R^1$ and $R^3$ may be attached to each other to form a 5- to 7-membered ring, but do not form a 2,2,6,6-tetraalkylpiperidine skeleton; provided that $R^1$ and $R^2$ are not simultaneously hydrogen atoms and have a total of 7 or more carbon atoms, and in formula (TS-II), $R^4$ to $R^7$ represent a hydrogen atom, an alkyl group having 1 to 20 carbon atoms, or an aryl group having 6 to 15 carbon atoms.

16. The set of resin compositions for covering a flexible tube substrate for an endoscope according to claim 15, wherein a ratio of an amount of the hindered amine compound (b) to an amount of the compound (c) is 1:50 to 50:1 by mass.

17. The flexible tube for an endoscope according to claim 1, wherein, in formula (TS-I), $R^3$ represents an unsubstituted aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, a hydroxy group or an aliphatic group to which a halogen atom, an aryl group, a heterocyclic group, a cyano group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an unsubstituted amino group, an alkylamino group, an anilino group, a formylamino group, an unsubstituted alkylcarbonylamino group, an arylcarbonylamino group, an aminocarbonylamino group, an alkoxycarbonylamino group, an aryloxycarbonylamino group, a sulfamoylamino group, an alkylsulfonylamino group, an arylsulfonylamino group, a sulfanyl group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imide group, a phosphino group, a phosphinyl group, a phosphinyloxy group, a phosphinylamino group, or a silyl group bind.

18. The flexible tube for an endoscope according to claim 13, wherein, in formula (TS-I), $R^3$ represents an unsubstituted aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, a hydroxy group or an aliphatic group to which a halogen atom, an aryl group, a heterocyclic group, a cyano group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an unsubstituted amino group, an alkylamino group, an anilino group, a formylamino group, an unsubstituted alkylcarbonylamino group, an arylcarbonylamino group, an aminocarbonylamino group, an alkoxycarbonylamino group, an aryloxycarbonylamino group, a sulfamoylamino group, an alkylsulfonylamino group, an arylsulfonylamino group, a sulfanyl group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imide group, a phosphino group, a phosphinyl group, a phosphinyloxy group, a phosphinylamino group, or a silyl group bind.

19. The flexible tube for an endoscope according to claim 15, wherein, in formula (TS-I), $R^3$ represents an unsubstituted aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, a hydroxy group or an aliphatic group to which a halogen atom, an aryl group, a heterocyclic group, a cyano group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an unsubstituted amino group, an alkylamino group, an anilino group, a formylamino group, an unsubstituted alkylcarbonylamino group, an arylcarbonylamino group, an aminocarbonylamino group, an alkoxycarbonylamino group, an aryloxycarbonylamino group, a sulfamoylamino group, an alkylsulfonylamino group, an arylsulfonylamino group, a sulfanyl group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imide group, a phosphino group, a phosphinyl group, a phosphinyloxy group, a phosphinylamino group, or a silyl group bind.

\* \* \* \* \*